(12) United States Patent
D'Andrea et al.

(10) Patent No.: US 11,224,608 B2
(45) Date of Patent: Jan. 18, 2022

(54) COMPOUNDS AND METHODS FOR TREATING CANCER

(71) Applicant: Dana-Farber Cancer Institute, Inc., Boston, MA (US)

(72) Inventors: Alan D'Andrea, Winchester, MA (US); Raphael Ceccaldi, Paris (FR); Jia Zhou, Natick, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 44 days.

(21) Appl. No.: 16/643,689

(22) PCT Filed: Oct. 16, 2018

(86) PCT No.: PCT/US2018/056080
§ 371 (c)(1),
(2) Date: Mar. 2, 2020

(87) PCT Pub. No.: WO2019/079297
PCT Pub. Date: Apr. 25, 2019

(65) Prior Publication Data
US 2021/0154219 A1    May 27, 2021

Related U.S. Application Data

(60) Provisional application No. 62/572,977, filed on Oct. 16, 2017.

(51) Int. Cl.
*A61K 31/7048* (2006.01)
*C07H 15/20* (2006.01)
(Continued)

(52) U.S. Cl.
CPC ........ *A61K 31/7048* (2013.01); *A61K 31/357* (2013.01); *A61K 31/704* (2013.01);
(Continued)

(58) Field of Classification Search
None
See application file for complete search history.

(56) References Cited

U.S. PATENT DOCUMENTS 5,304,121 A  4/1994  Sahatjian
5,747,282 A  5/1998  Skolnick et al.
(Continued)

FOREIGN PATENT DOCUMENTS

EP  2710142  5/2012
WO  WO 1998/043092  10/1998
(Continued)

OTHER PUBLICATIONS

Hoppe et al., "Biomarkers for Homologous Recombination Deficiency in Cancer" J Natl Cancer Inst vol. 110 No. 7 pp. 704-713 doi: 10.1093/jnci/djy085 (Year: 2018).*
(Continued)

*Primary Examiner* — Eric Olson
(74) *Attorney, Agent, or Firm* — Fish & Richardson P.C.

(57) ABSTRACT

The present application provides, in some aspects, methods of treating cancers, such as homologous recombination (HR)-deficient cancers. In some embodiments, the disclosure provides a method for treating cancer by administering to a subject a compound of Formula (I):(I), or a pharmaceutically acceptable salt thereof.

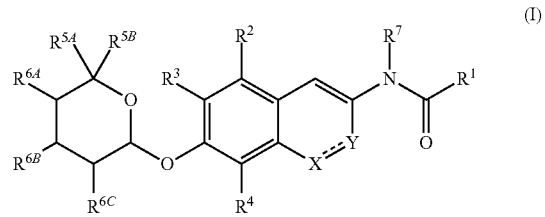

45 Claims, 15 Drawing Sheets

(51) Int. Cl.

| | | |
|---|---|---|
| *A61K 31/704* | (2006.01) | |
| *C07H 17/07* | (2006.01) | |
| *C07H 17/02* | (2006.01) | |
| *A61K 31/706* | (2006.01) | |
| *C07H 17/075* | (2006.01) | |
| *A61K 33/243* | (2019.01) | |
| *A61K 31/357* | (2006.01) | |
| *A61K 45/06* | (2006.01) | |
| *A61P 35/00* | (2006.01) | |

(52) U.S. Cl.
CPC .......... *A61K 31/706* (2013.01); *A61K 33/243* (2019.01); *A61K 45/06* (2013.01); *A61P 35/00* (2018.01); *C07H 15/20* (2013.01); *C07H 17/02* (2013.01); *C07H 17/07* (2013.01); *C07H 17/075* (2013.01)

(56) References Cited

U.S. PATENT DOCUMENTS

| | | |
|---|---|---|
| 5,837,492 A | 11/1998 | Tavtigian et al. |
| 5,886,026 A | 3/1999 | Hunter et al. |
| 6,083,698 A | 7/2000 | Olson et al. |
| 6,099,562 A | 8/2000 | Ding et al. |
| 6,803,031 B2 | 10/2004 | Rabinowitz et al. |
| 7,208,630 B2 | 4/2007 | Blagg et al. |
| 7,250,497 B2 | 7/2007 | Scholl et al. |
| 7,605,288 B2 | 10/2009 | Blagg et al. |
| 7,608,594 B2 | 10/2009 | Blagg et al. |
| 7,622,451 B2 | 11/2009 | Blagg et al. |
| 7,811,998 B2 | 10/2010 | Blagg et al. |
| 7,960,353 B2 | 6/2011 | Blagg |
| 8,188,306 B2 | 5/2012 | Blagg et al. |
| 8,212,011 B2 | 7/2012 | Blagg |
| 8,212,012 B2 | 7/2012 | Blagg |
| 8,729,048 B2 | 5/2014 | Kaufmann et al. |
| 9,120,774 B2 | 9/2015 | Blagg et al. |
| 10,030,006 B2 | 7/2018 | Blagg et al. |
| 2003/0235819 A1 | 12/2003 | Rabin |
| 2009/0163709 A1 | 6/2009 | Blagg |
| 2010/0048882 A1 | 2/2010 | Blagg et al. |
| 2012/0022026 A1* | 1/2012 | Krawczyk ............... A61P 35/00 514/152 |
| 2016/0272584 A1 | 9/2016 | Blagg et al. |
| 2016/0289217 A1 | 10/2016 | Blagg et al. |

FOREIGN PATENT DOCUMENTS

| | | |
|---|---|---|
| WO | WO 1999/028506 | 6/1999 |
| WO | WO 2006/047740 | 5/2006 |
| WO | WO 2006/050501 | 5/2006 |
| WO | WO 2010/096650 | 8/2010 |
| WO | WO 2011/153345 | 12/2011 |
| WO | WO 2013/124740 | 8/2013 |
| WO | WO 2014/138101 | 9/2014 |
| WO | WO 2014/160876 | 10/2014 |
| WO | WO 2014/205105 | 12/2014 |
| WO | WO 2015/040378 | 3/2015 |
| WO | 2017/070198 | 4/2017 |

OTHER PUBLICATIONS

Dungey et al., "Enhanced radiosensitization of human glioma cells by combining inhibition of poly(ADP-ribose) polymerase with inhibition of heat shock protein 90" Mol Cancer Ther vol. 8 No. 8 pp. 2243-2254, DOI: 10.1158/1535-7163.MCT-09-0201 (Year: 2009).*
Ame et al., "The PARP Superfamily," Bioessays, 2004, 26:882-893.
Bast et al., "The Biology of Ovarian Cancer: New Opportunities for Translation," Nature reviews Cancer, 2009, 9:415-428.
Brody, "Treating Cancer by Targeting a Weakness," The New England journal of medicine, 2005, 353:949-950.
Ceccaldi et al., "Homologous-recombination-deficient Tumours Are Dependent on Po10-mediated Repair," Nature, 2015, 518:258-262.
D'Andrea, "Susceptibility Pathways in Fanconi's Anemia and Breast Cancer," N Engl J Med., 2010, 362:1909-1919.
Dantzer et al., "Poly(ADP-ribose) polymerase-1 Activation During DNA Damage and Repair," Methods Enzymol., 2006, 409:493-510.
Donnelly et al, "The Design, Synthesis, and Evaluation of Coumarin Ring Derivatives of the Novobiocin Scaffold that Exhibit Antiproliferative Activity," Journal of Organic Chemistry, 2008, 73:8901-8920.
Eder et al., "A Phase I Clinical Trial of Novobiocin, a Modulator of Alkylating Agent Cytotoxicity," Cancer Research, 1991, 51(2):510-13.
Evers et al., "Targeting Homologous Recombination Repair Defects in Cancer," Trends Pharmacol Sci., 2010, 31(8):372-80.
Farmer et al., "Targeting the DNA Repair Defect in BRCA Mutant Cells as a Therapeutic Strategy," Nature, 2005, 434:917-921.
Friend et al., "Breast Cancer Information on the Web," Nature Genetics, 1995, 11:238.
Helleday, "Homologous Recombination in Cancer Development, Treatment and Development of Drug Resistance," Carcinigenesis, 2010, 21(6):955-960.
Illum, "Is Nose-To-Brain Transport of Drugs in Man a Reality?" J Pharm Pharmacol, 2004, 56:3-17.
Illum, "Transport of Drugs From the Nasal Cavity to the Central Nervous System," Eur J Pharm Sci, 2000, 11:1-18.
Mateos-Gomez et al., "Mammalian Polymerase Theta Promotes Alternative NHEJ and Suppresses Recombination," Nature, 2015, 518:254-257.
McCabe et al., "Deficiency in the Repair of DNA Damage by Homologous Recombination and Sensitivity to Poly(ADP-Ribose) Polymerase Inhibition," Cancer research, 2006, 66:8109-8115.
Miki et al., "A strong candidate for the breast and ovarian cancer susceptibility gene BRCA1," Science, 1994, 266:66-71.
Montoni et al., "Resistance to PARP-Inhibitors in Cancer Therapy," Front Pharmacol., 2013, 27:4:18.
Mukhopadhyay et al., "Development of a Functional Assay for Homologous Recombination Status in Primary Cultures of Epithelial Ovarian Tumor and Correlation With Sensitivity to poly(ADP-ribose) Polymerase Inhibitors," Clin. Cancer Res., 2010, 16:2344-2351.
Pal et al., "BRCA1 and BRCA2 Mutations Account for a Large Proportion of Ovarian Carcinoma Cases," Cancer, 2005, 104:2807-2816.
PCT International Preliminary Report on Patentability in Appln. No. PCT/US2018/056080, dated Apr. 21, 2020, 10 pages.
Pignata et al., "Chemotherapy in Epithelial Ovarian Cancer ," Cancer letters, 2011, 303:73-83.
Seki et al., "POLQ (Pol Theta), a DNA Polymerase and DNA-dependent ATPase in Human Cells," Nucl. Acids Res., 2003, 31(21):6117-6126.
Shen et al., "Cisplatin Resistance: A Cellular Self-Defense Mechanism Resulting From Multiple Epigenetic and Genetic Changes," Pharmacol Rev, 2012, 64:706-721.
Shima et al., "The Mouse Genomic Instability Mutation chaos1 Is an Allele of Polq That Exhibits Genetic Interaction With Atm," Molecular and cellular biology, 2004, 24:10381-10389.
Siegel et al., "Cancer Statistics, 2017," CA Cancer J Clin, 2017, 67:7-30.
Sung et al., "Mechanism of homologous recombination: mediators and helicases take on regulatory functions," Nature Reviews Molecular Cell Biology, 2006, 7(10):739-750.
Wooster et al., "Identification of the Breast Cancer Susceptibility Gene BRCA2," Nature, 1995, 378:789-792.
ISA/US, International Search Report issued for PCT/US2018/056080 (dated Dec. 14, 2018).
Kent, T. et al., "DNA polymerase theta specializes in incorporating synthetic expanded-size (xDNA) nucleotides." Nucleic Acids Research 44(19) (2016); published online Sep. 2, 2016, pp. 9381-9392; abstract.
Donnelly, Alison C., et al., "The Design, Synthesis, and Evaluation of Coumarin Ring Derivatives of the Novobiocin Scaffold that Exhibit Antiproliferative Activity," J. Org. Chem. 73:8901-8920 (2008).

(56) References Cited

OTHER PUBLICATIONS

Allen et al., "Impact of sequencing of androgen receptor-signaling inhibition (ARSI) and ionizing radiotherapy (RT) in prostate cancer: importance of homologous recombination (HR) disruption," International Journal of Radiation, Oncology, Biology, Physics, Oct. 23, 2020, 108(3S):e853, 1 page.
Extended European Search Report in European Appln. No. 18868494.8, dated Aug. 2, 2021, 10 pages.
Kachhap et al., "Downregulation of homologous recombination DNA repair genes by HDAC inhibition in prostate cancer is mediated through the E2F1 transcription factor," PloS one. Jun. 2010, 5(6):e11208, 12 pages.
Shahar et al., "A high-throughput chemical screen with FDA approved drugs reveals that the antihypertensive drug Spironolactone impairs cancer cell survival by inhibiting homology directed repair," Nucleic Acids Research, May 14, 2014, 42(9):5689-701 and supplementary data, 31 pages.

* cited by examiner

COMPOUNDS AND METHODS FOR TREATING CANCER

CROSS-REFERENCE TO RELATED APPLICATIONS

This application is a national phase filing under 35 U.S.C. § 371 of International application number PCT/US2018/056080, filed Oct. 16, 2018, which claims the benefit of priority of U.S. Provisional Appl. No. 62/572,977, filed Oct. 16, 2017, the contents of which are incorporated by reference in their entirety herein.

TECHNICAL FIELD

This invention relates to compounds useful in treating cancer, in particular to chromen-2-one, naphthalene and quinoline derivatives useful in treating cancer identified as having a homologous recombination (HR) deficiency.

BACKGROUND

Large-scale genomic studies have shown that half of epithelial ovarian cancers (EOCs) have alterations in genes regulating homologous recombination (HR) repair. Loss of HR accounts for the genomic instability of EOCs and for their cellular hyper-dependence on alternative poly-ADP ribose polymerase (PARP)-mediated DNA repair mechanisms. PARP inhibitors (PARPi) can be used to treat some HR-deficient cancers. However, certain cancers are resistant to treatment with PARP inhibitors. Accordingly, there is a general need to develop novel methods of regulating DNA repair mechanisms for the treatment of HR-deficient cancer.

SUMMARY

Cancer cells are often defective in one of the six major DNA repair pathways. As an example, approximately half of the epithelial ovarian cancers (EOCs) have alterations in genes regulating homologous recombination (HR), which accounts for their genomic instability and poly(ADP-ribose) polymerase inhibitor (PARPi) sensitivity. Several other solid tumor types, including breast, prostate, and pancreatic cancers, also often have HR defects. POLQ, a translesion DNA polymerase that is involved in alternative end joining (Alt-EJ), regulates genomic stability in HR-deficient cancers. For example, loss of POLQ-mediated DNA repair in HR-deficient ovarian cancer cells creates a synthetic lethality (Ceccaldi et al., 2015).

In a first general aspect, the present disclosure provides a method of treating a homologous recombination (HR)-deficient cancer, the method comprising administering to a subject in need thereof (e.g., a patient) a therapeutically effective amount of a compound of Formula (I), or a pharmaceutically acceptable salt thereof. In some embodiments, the method further comprises, before administering the compound to the patient, determining that the HR-deficient cancer contains a mutation or an alteration in a gene regulating homologous recombination. In some embodiments, the gene regulating homologous recombination is BRCA1/2. In some embodiments, the cancer is selected from prostate cancer, colon cancer, lung cancer, liver cancer, sarcoma, melanoma, breast cancer, ovarian cancer, and pancreatic cancer.

In a second general aspect, the present disclosure provides a method of treating a cancer selected from ovarian cancer and pancreatic cancer, the method comprising administering to a subject in need thereof a therapeutically effective amount of a compound of Formula (I), or a pharmaceutically acceptable salt thereof.

Implementations of the first and second general aspects can include one or more of the following features. In some embodiments, the method further comprises administering to the subject a therapeutically effective amount of an additional anti-cancer agent. In some embodiments, the additional anti-cancer agent is a platinum-based anti-cancer agent. In some embodiments, the platinum-based anti-cancer agent is selected from carboplatin and cisplatin. In some embodiments, the additional anti-cancer agent is a PARP inhibitor. In some embodiments, the PARP inhibitor is selected from olaparib, veliparib, BGB-290, talazoparib, BMN 673, and niraparib.

In a third general aspect, the present disclosure provides a method of inhibiting DNA polymerase θ (Polθ) in a cancer cell, the method comprising contacting the cancer cell with an effective amount of a compound of Formula (I), or a pharmaceutically acceptable salt thereof. In some embodiments, the cancer cell is contacted in vitro. In some embodiments, the cancer cell is contacted in vivo. In some embodiments, the cancer cell is contacted ex vivo.

Implementations of the first, second, and third general aspects can include one or more of the following features.

In some embodiments, the compound of Formula (I) is selected from the group consisting of:

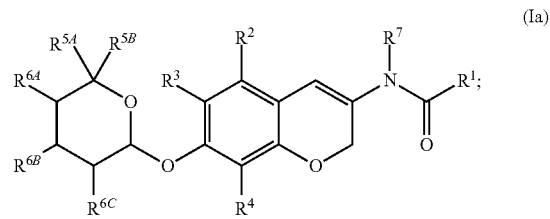

(Ia)

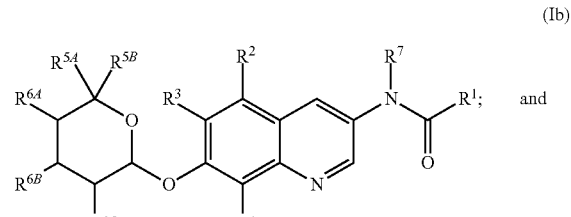

(Ib) and

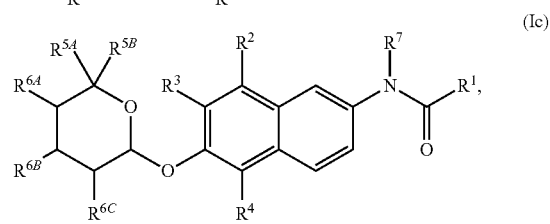

(Ic)

or a pharmaceutically acceptable salt thereof.

In some embodiments, $R^1$ is selected from the group consisting of: $C_{1-6}$ alkyl, $C_{6-12}$ aryl and 5-10 membered heteroaryl, each of which is optionally substituted by 1 or 2 groups independently selected from the group consisting of: $Cy^1$ and $R^g$.

In some embodiments, $R^1$ is $C_{1-6}$ alkyl.

In some embodiments, $R^1$ is 5-10 membered heteroaryl.

In some embodiments, $R^1$ is $C_{6-12}$ aryl, optionally substituted by 1 or 2 groups independently selected from the group consisting of: $Cy^1$ and $R^g$.

In some embodiments, $R^1$ is selected from the group consisting of: methyl, 3-(3-methylbut-2-en-1-yl)-4-hydroxyphenyl, 3',6-dimethoxy-[1,1'-biphenyl-3-yl], and indol-2-yl.

In some embodiments, $R^2$ and $R^3$ are independently selected from the group consisting of: H and $C_{1-6}$ alkoxy.

In some embodiments, $R^2$ and $R^3$ are each H.

In some embodiments, $R^2$ is H and $R^3$ is $C_{1-6}$ alkoxy.

In some embodiments, $R^2$ is $C_{1-6}$ alkoxy and $R^3$ is H.

In some embodiments, $R^2$ and $R^3$ are independently selected from the group consisting of: H, methoxy, propoxy, and isopropoxy.

In some embodiments, $R^4$ is selected from the group consisting of: H, $C_{1-6}$ alkyl, $C_{6-12}$ aryl, and $C_{6-12}$ aryl-$C_{1-3}$ alkylene.

In some embodiments, $R^4$ is selected from the group consisting of: H, methyl, ethyl, phenyl, and benzyl.

In some embodiments, $R^{5A}$ and $R^{5B}$ are each $C_{1-3}$ alkyl.

In some embodiments, $R^{5A}$ and $R^{5B}$ are each methyl.

In some embodiments, $R^{6A}$, $R^{6B}$ and $R^{6C}$ are independently selected from the group consisting of: OH, $C_{1-6}$ alkoxy, and $C(=O)NR^{a1}R^{a2}$.

In some embodiments, $R^{6A}$ is $C_{1-6}$ alkoxy.

In some embodiments, $R^{6B}$ is selected from the group selected from: OH and $C(=O)NR^{a1}R^{a2}$.

In some embodiments, $R^{6B}$ is selected from the group selected from: OH and $C(=O)NH_2$.

In some embodiments, $R^{6C}$ is OH.

In some embodiments, $R^7$ is selected from the group consisting of: H and $C_{1-6}$ alkyl, wherein the $C_{1-6}$ alkyl is optionally substituted with $Cy^1$.

In some embodiments, $R^7$ is selected from the group consisting of: H and 4-methoxy benzyl.

In some embodiments, $R^7$ is H.

In some embodiments, $Cy^1$ is $C_{6-12}$ aryl, optionally substituted by 1 or 2 independently selected $R^g$ groups.

In some embodiments, $Cy^1$ is phenyl, optionally substituted with $R^g$.

In some embodiments, $Cy^1$ is selected from the group consisting of: 3-methoxyphenyl and 4-methoxyphenyl.

In some embodiments, $R^g$ is selected from the group consisting of: OH, $C_{2-6}$ alkenyl, and $C_{1-6}$ alkoxy.

In some embodiments, $R^g$ is selected from the group consisting of: OH, 3-methylbut-2-en-1-yl, and methoxy.

In some embodiments:
$R^1$ is selected from the group consisting of: $C_{1-6}$ alkyl, $C_{6-12}$ aryl and 5-10 membered heteroaryl, each of which is optionally substituted by 1 or 2 groups independently selected from the group consisting of: $Cy^1$ and $R^g$;

$R^2$ and $R^3$ are independently selected from the group consisting of: H and $C_{1-6}$ alkoxy;

$R^4$ is selected from the group consisting of: H, $C_{1-6}$ alkyl, $C_{6-12}$ aryl, and $C_{6-12}$ aryl-$C_{1-3}$ alkylene;

$R^{5A}$ and $R^{5B}$ are each $C_{1-3}$ alkyl;

$R^{6A}$, $R^{6B}$ and $R^{6C}$ are independently selected from the group consisting of: OH, $C_{1-6}$ alkoxy, and $C(=O)NR^{a1}R^{a2}$;

$R^7$ is selected from the group consisting of: H and $C_{1-6}$ alkyl, wherein the $C_{1-6}$ alkyl is optionally substituted with $Cy^1$;

$Cy^1$ is $C_{6-12}$ aryl, optionally substituted by 1 or 2 independently selected $R^g$ groups; and $R^g$ is selected from the group consisting of: OH, $C_{2-6}$ alkenyl, and $C_{1-6}$ alkoxy.

In some embodiments:
$R^1$ is selected from the group consisting of: methyl, indol-2-yl, and phenyl, wherein the phenyl is optionally substituted by 1 or 2 groups independently selected from the group consisting of: $Cy^1$ and $R^g$;

$R^2$ and $R^3$ are independently selected from the group consisting of: H, methoxy, propoxy, and isopropoxy;

$R^4$ is selected from the group consisting of: H, methyl, ethyl, phenyl, and benzyl;

$R^{5A}$ and $R^{5B}$ are each methyl;

$R^{6A}$ is $C_{1-6}$ alkoxy;

$R^{6B}$ is selected from the group selected from: OH and $C(=O)NH_2$;

$R^{6C}$ is OH;

$R^7$ is selected from the group consisting of: H and $C_{1-6}$ alkyl substituted with $Cy^1$;

$Cy^1$ is phenyl, optionally substituted with $R^g$; and $R^g$ is selected from the group consisting of: OH, 3-methylbut-2-en-1-yl, and methoxy.

In some embodiments, the compound of Formula (I) is selected from any one of the compounds described herein.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DESCRIPTION OF DRAWINGS

FIG. 5 DETAILED DESCRIPTION

Figure 1:
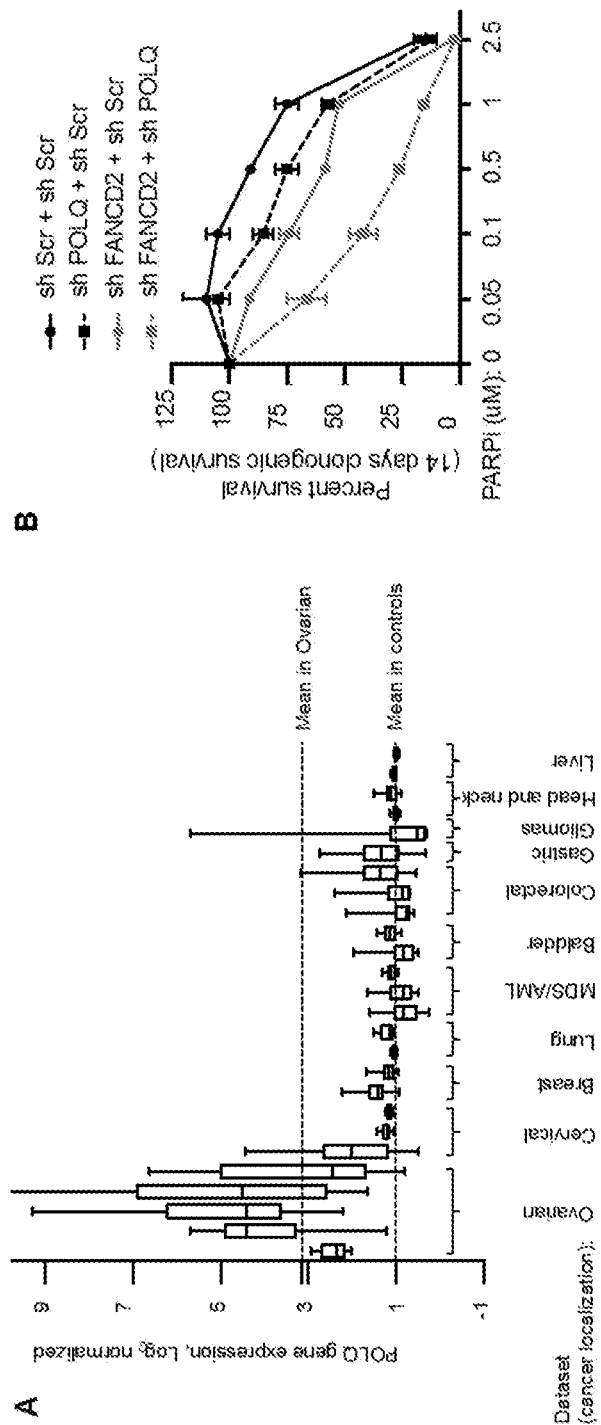
FIG. 1A. is a plot showing POLQ expression in different cancer localizations. POLQ expression values are normalized to the mean expression in control samples, which was arbitrarily attributed to 1. Each box plot represents the level of POLQ expression for one dataset.
FIG. 1B is a line plot showing Knockdown POLQ in HR-deficient cells (shFANCD2) sensitize cells to PARP inhibitor. POLQ and/or FANCD2 depleted cells were treated with increasing concentration of PARPi for a 14 days clonogenic survival assay. Error bars show standard error of the mean, n=3.
Figure 2:
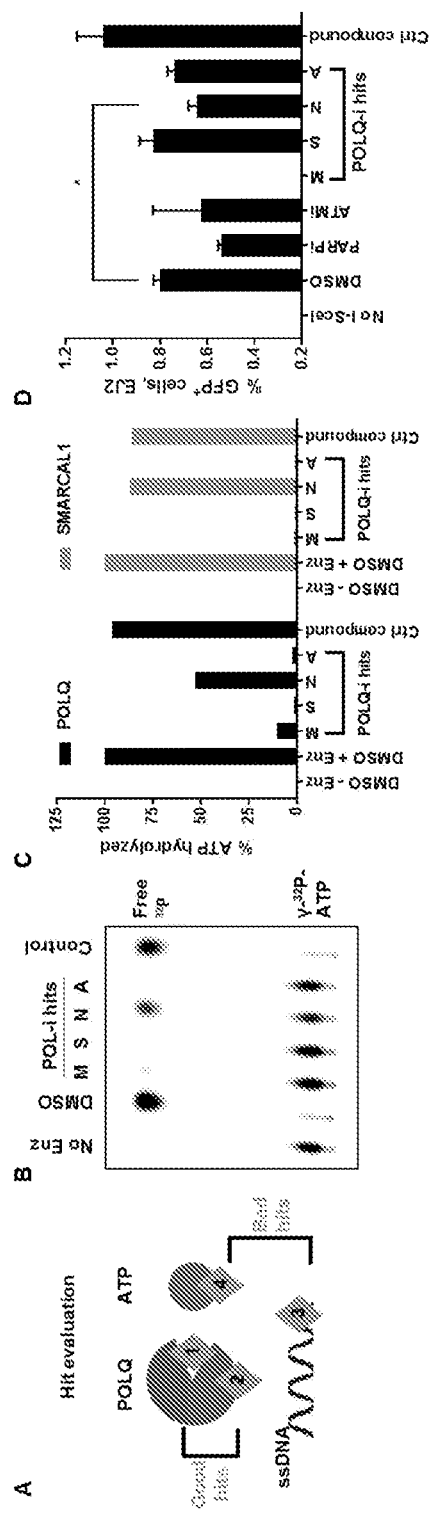
FIG. 2A is an image showing various mechanisms of inhibiting the activity of POLQ.
FIG. 2B is a representative image of γ-32p-ATP based radiometric ATPase assay, showing compounds M, S, N (novobiocin), A inhibited POLQ activity.
FIG. 2C is a bar plot showing quantification of the radiometric ATPase assay showing in FIG. 2B. SMARCAL1 was used as a control ATPase to identify inhibitors that show specificity to POLQ. Compound N (novobiocin) showed some specificity to POLQ.
FIG. 2D is a bar graph showing GFP reporter assay using EJ2 repair substrate to test if the hits specifically inhibit the Alt-EJ repair pathway. Compound N (novobiocin) inhibited Alt-EJ. PARP inhibitor and ATM inhibitor were used as positive controls.
Figure 3:
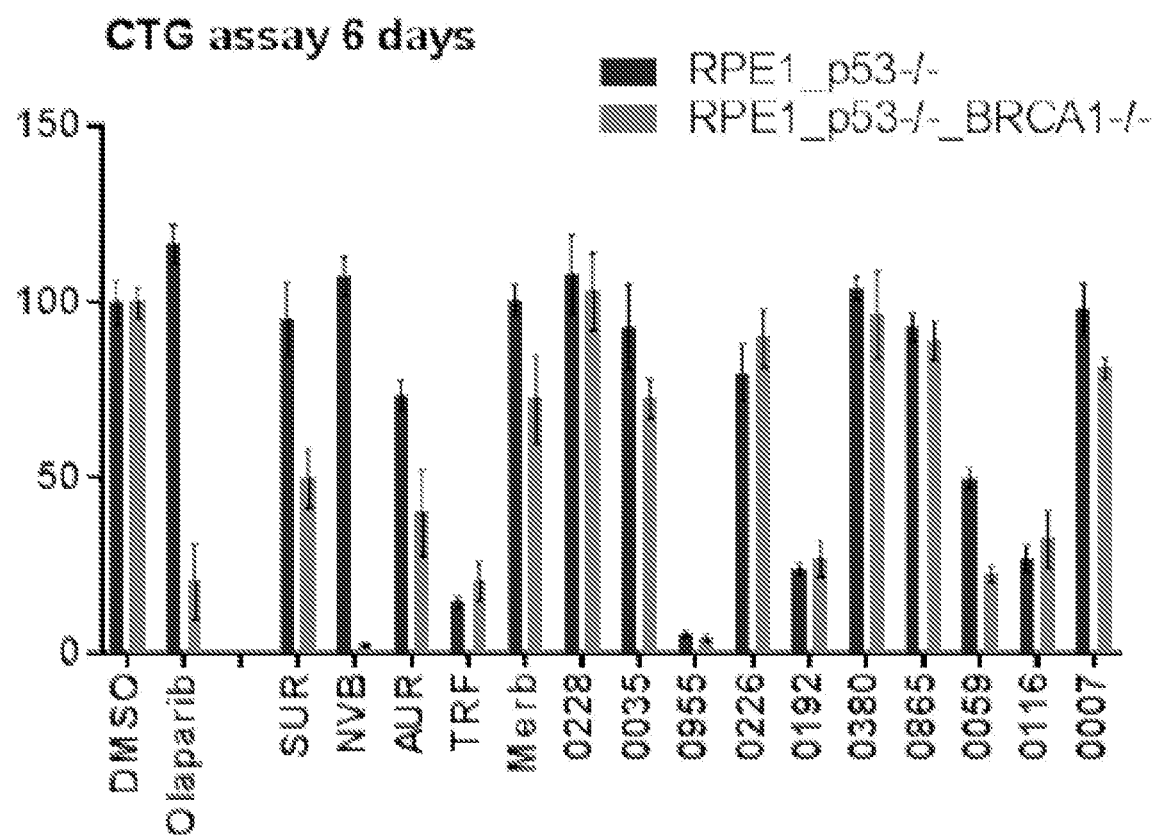
FIG. 3 is a bar plot showing results of Rapid Cell Titer Glo assay indicating that novobiocin (NVB), like the PARP inhibitor olaparib, selectively kills BRCA1-deficient (HR-deficient) tumor cells.
Figure 4:
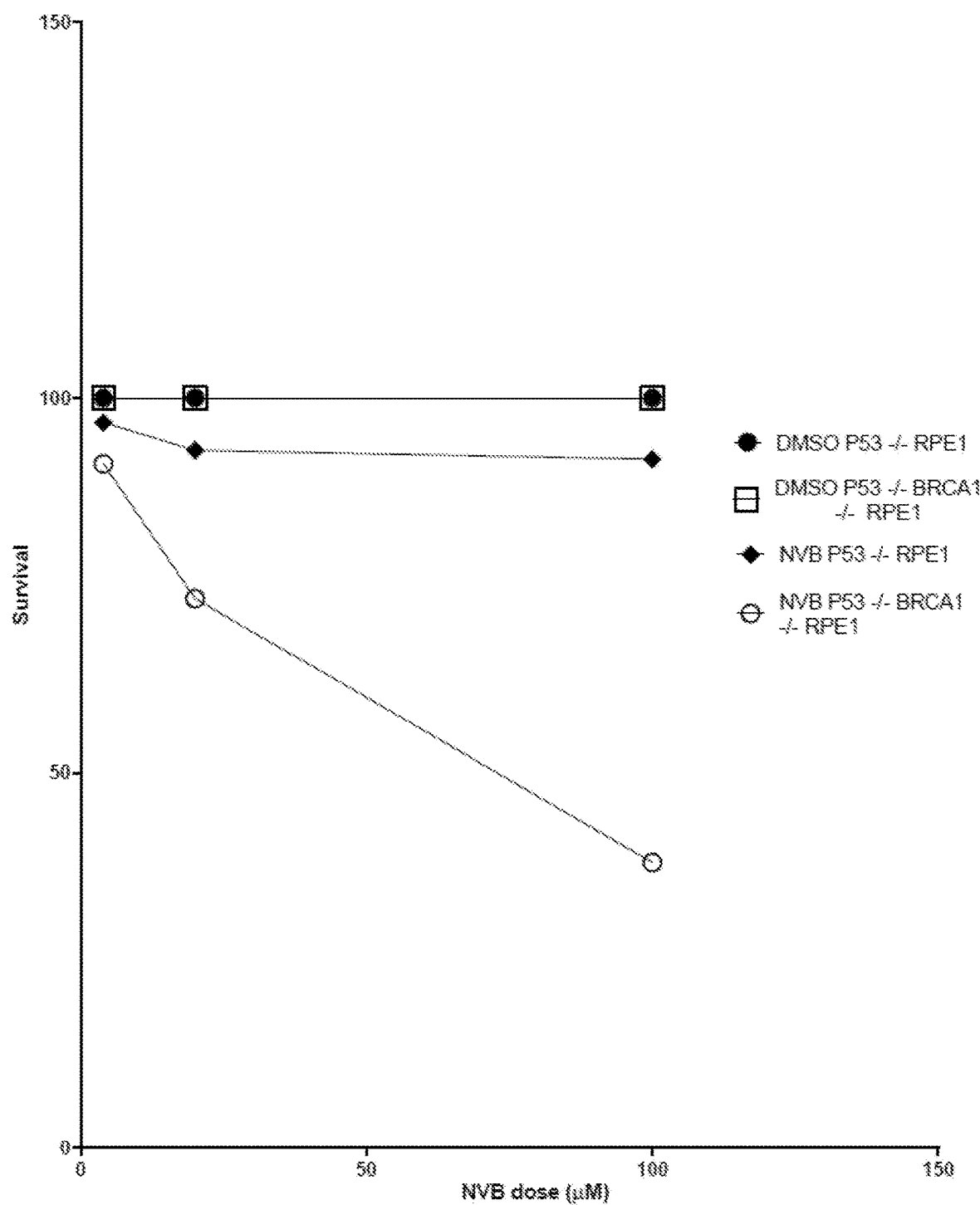
FIG. 4 is a line plot showing results of clonogenic survival assay indicating that novobiocin (NVB) selectively kills the BRCA1-deficient tumor cells.

In one general aspect, the present disclosure provides a method of treating cancer, the method comprising administering to a subject (e.g., in need thereof) a therapeutically effective amount of a compound of Formula (I) as described herein, or a pharmaceutically acceptable salt thereof. In some embodiments, the cancer is homologous recombination (HR)-deficient.

The HR-deficiency in a cancer can be characterized by a lack of a functional homologous recombination (HR) DNA repair pathway, and can be correlated with mutation or alteration of one or more HR-associated genes, such as BRCA1, BRCA2, RAD50, RAD54, RAD51B, RAD51C, RAD51D, Ct1P (Choline Transporter-Like Protein), PALB2 (Partner and Localizer of BRCA2), XRCC2 (X-ray repair complementing defective repair in Chinese hamster cells 2), RECQL4 (RecQ Protein-Like 4), BLM (Bloom syndrome, RecQ helicase-like), WRN (Werner syndrome, RecQ helicase-like), Nbsl (Nibrin), and genes encoding Fanconi anemia (FA) proteins or FA-like genes. Examples of FA and FA-like genes include FANCA/C/D2/E//F//GL, FANCA, FANCB, FANCC, FANCD1 (BRCA2), FANCD2, FANCE, FANCF, FANCG FANCI, FANCJ (BRIP1), FANCL, FANCM, FANCN (PALB2), FANCP (SLX4), FANCS (BRCA1), RAD51C, and XPF. Other suitable examples of HR-associated genes include RECA, ARID1A, ATM, CHEK1/2, FAM175A, HDAC2, ERCC3, MRE11A, CDK12, CDKN1A/B/C, BAP1, MLL2, CDKN2A, NPM1, TP53, ATRX, BARD1, BRCA1/2, BRIP1, MRE11A, NBN, PTEN, and ATR. In some embodiments, a cancer known to have a mutation in at least one HR-associated gene is an HR-deficient cancer. In some embodiments, the mutation is a pathogenic somatic mutation. In other embodiments, the mutation is germline mutation. In some embodiments, an HR-deficient cancer has at least one mutated HR gene selected from PTEN, BRCA1, BRCA2, and ATM.

In some embodiments, the cancer is characterized by one or more BRCA mutations. In some aspects of these embodiments, the cancer is characterized by BRCA1 mutation, BRCA2 mutation, or a mutation in both BRCA1 and BRCA2 genes.

Located on chromosome 17, BRCA1 is the first gene identified conferring increased risk for breast and ovarian cancer (Miki et al., Science, 266:66-71 (1994)). The BRCA1 gene (Gene ID: 672) is divided into 24 separate exons. Exons 1 and 4 are noncoding, in that they are not part of the final functional BRCA1 protein product. The BRCA1 coding region spans roughly 5600 base pairs (bp). Each exon consists of 200-400 bp, except for exon 11 which contains about 3600 bp.

Wooster et al. (Nature 378: 789-792, 1995) identified the BRCA2 gene by positional cloning of a region on chromosome 13q12-q13 implicated in Icelandic families with breast cancer. Human BRCA2 (Gene ID: 675) gene contains 27 exons. Similar to BRCA1, BRCA2 gene also has a large exon 11, translational start sites in exon 2, and coding sequences that are AT-rich.

Mutations of BRCA genes associated with cancer (i.e., predisposing the subject to developing cancer) are described, for example, in Friend, S. et al., 1995, Nature Genetics 11: 238, US 2003/0235819, U.S. Pat. Nos. 6,083, 698, 7,250,497, 5,747,282, WO 1999028506, U.S. Pat. No. 5,837,492, WO 2014160876; all of which are incorporated herein by reference.

POLO Upregulation in Cancer

Without being bound by any particular theory, it is believed that an inverse correlation exists between homologous recombination (HR) deficiency and levels of DNA polymerase θ (Polθ) expression in cancer cells. DNA polymerase θ (Pol9, also referred to as POLQ; Gene ID No. 10721) is a family A DNA polymerase that also functions as a DNA-dependent ATPase (see, e.g., Seki et al. Nucl. Acids Res. (2003) 31 (21): 6117-6126). Since HR-deficient cancers lack a functional DNA repair pathway, an increase in the expression POLQ in HR-deficient cancer is believed to be compensatory, i.e., increased levels of POLQ regulate genomic stability and survival in these cancers. It is believed that HR-deficient tumors with repair deficiency, which often exhibit replication stress and collapsed replication forks, are hyper-dependent on alternative repair pathways and upregulate POLQ expression as a survival mechanism (See, e.g., Ceccaldi et al., 2015).

For example, POLQ is implicated in a pathway required for the repair of double-stranded DNA breaks, referred to as the error-prone microhomology-mediated end-joining (MMEJ) pathway. POLQ is also a translesion polymerase that is involved in alternative end joining (Alt-EJ) of double-stranded breaks (DSB) (Ceccaldi et al., 2015, Nature 518, 258-262; Mateos-Gomez et al., 2015, Nature 518, 254-257). Knockdown of POLQ was found to enhance cell death in HR-deficient cancers. For example, POLQ deletion in a HR-deficient background, such as Atm−/− or Fancd2−/−, results in marked developmental disadvantage or synthetic embryonic lethality in mice (Ceccaldi et al., 2015, Nature 518, 258-262; Shima et al., 2004, Molecular and cellular biology 24, 10381-10389). In another example, knockdown of POLQ in HR-proficient cells up-regulates HR activity and RAD51 nucleofilament assembly, while knockdown of POLQ in HR-deficient EOCs enhances cell death (See, e.g., Ceccaldi et al., Nature (2015) 518, 7538, 258-262).

In some embodiments, the cancer (e.g., HR-deficient cancer as described herein) has upregulated expression (e.g., overexpression) of POLQ. In some embodiments, POLQ overexpression in the cancer can be at least 2-fold, at least 3-fold, at least 4-fold, at least 5-fold, at least 10-fold, at least 20-fold, at least 50-fold, at least 100-fold, at least 500-fold, or at least 1000-fold greater, relative to POLQ expression in a control tissue (e.g., anon-cancer cells of the same type).

In some embodiments, the compound of Formula (I), or a pharmaceutically acceptable salt thereof, is an inhibitor of POLQ. That is, the compound of Formula (I) reduces, slows, halts, and/or prevents POLQ activity in a cancer cell (e.g., HR-deficient cancer cell). POLQ is a large protein containing an N-term helicase-like ATPase domain, a central linker domain, and a C-term polymerase domain. It has been shown that both the ATPase domain and the polymerase domain are required for POLQ-mediated Alt-EJ (Beagan et al., 2017, PLoS Genet 13, e1006813). In some embodiments, the compound of Formula (I) inhibits polymerase function, ATPase function, or polymerase function and ATPase function of POLQ. In some embodiments, the compound of Formula (I) disrupts POLQ-DNA interaction or antagonizes ATP. In some embodiments, the compound of formula (I) selectively inhibits (e.g., reduces, slows, halts, and/or prevents) the ATPase activity of POLQ. In some aspects of these embodiments, the compound of Formula (I) selectively inhibits ATPase activity of POLQ and does not inhibit the polymerase activity of POLQ or disrupt POLQ-DNA interactions. In some embodiments, the compound of Formula (I) selectively inhibits ATPase activity of POLQ and does not inhibit other ATPase enzymes in the cancer cell. In some embodiments, the compound of Formula (I) targets and selectively inhibits ATPase domain of POLQ and therefore promotes lethality of cancers, such as HR-deficient cancers, while having little or no effect on healthy cells.

In some embodiments, the present disclosure provides a method of inhibiting DNA polymerase θ (Polθ) in a cancer cell, the method comprising contacting the cancer cell with an effective amount of a compound of Formula (I), or a pharmaceutically acceptable salt thereof. In some embodiments, the cancer cell is HR-deficient as described herein. In some embodiments, the cancer cell is contacted in vitro, in vivo, or ex vivo. In some embodiments, POLQ is inhibited in a cancer cell of a patient after the compound of Formula (I), or a pharmaceutically acceptable salt thereof, is administered to the patient in need thereof.

In some embodiments, the present disclosure provides a method of treating cancer characterized by overexpression of DNA polymerase θ (Polθ), the method comprising administering to a subject in need thereof a therapeutically effective amount of a compound of Formula (I), or a pharmaceutically acceptable salt thereof. In some aspects of these embodiments, the cancer contains a mutation in at least one gene regulating homologous recombination (HR) (e.g., BRCA 1/2 gene), as described herein. Accordingly, aspects of the disclosure provide a method for treating cancer that is characterized by one or more HR-associated mutations and overexpressed POLQ.

Identifying Step

In some embodiments, a method of treating cancer described herein comprises the steps of: a) determining that the cancer contains a mutation or alteration in a gene regulating homologous recombination (HR); and b) administering to a subject in need thereof a therapeutically effective amount of a compound of Formula (I), or a pharmaceutically acceptable salt thereof. In some embodiments, a method of treating cancer described herein comprises the steps of: a) determining that the cancer is overexpressing POLQ; and b) administering to a subject in need thereof a therapeutically effective amount of a compound of Formula (I), or a pharmaceutically acceptable salt thereof. In any of the above embodiments, the administering of step b) occurs after the determining of step a); or the administering of step b) occurs prior to the determining of step a).

In some embodiments, a method of treating cancer described herein comprises the steps of: a) determining that the cancer contains a mutation or alteration in a gene regulating homologous recombination (HR); b) determining that the cancer is overexpressing POLQ; and c) administering to a subject in need thereof a therapeutically effective amount of a compound of Formula (I), or a pharmaceutically acceptable salt thereof. In some aspects of these embodiments, the administering of step c) occurs after the determining of steps a) and b); or the administering of step c) occurs before the determining of steps a) and b). In further aspects of these embodiments, the determining of step a) is conducted before the determining of step b); or the determining of step a) is conducted after the determining of step b).

In some embodiments, a mutation in a gene regulating homologous recombination, or the overexpression of POLQ can be determined without obtaining a cancer cell from a subject. For example, a mutation can be identified by analyzing blood sample of the subject, or a sample of hair, urine, saliva, or feces of the subject. In other embodiments, a mutation can be identified be obtaining a cancer cell from a subject. For example, a cancer cell for analysis of a mutation in an HR-associated gene or levels of expression of POLQ, can be obtained from the subject by surgical means (e.g., laparoscopically). In these embodiments, an HR mutation or a level of POLQ expression is being identified in the cancer cell of the subject.

Any of the methods, reagents, protocols and devices generally known in the art can be used to identify an HR mutation. For example, next generation sequencing, immunohistochemistry, fluorescence microscopy, break apart FISH analysis, Southern blotting, Western blotting, FACS analysis, Northern blotting, ELISA or ELISPOT, antibodies microarrays, or immunohistochemistry, and PCR-based amplification (e.g., RT-PCR and quantitative real-time RT-PCR) techniques can be used to identify the mutation or a POLQ status of cancer. As is well-known in the art, the assays are typically performed, e.g., with at least one labelled nucleic acid probe or at least one labelled antibody or antigen-binding fragment thereof. Assays can utilize other detection methods known in the art for detecting a mutation in a HR-associated gene. Any DNA sequencing platform for somatic mutations can be used. For example, Illumina MiSeq platform (Illumina TruSeq Amplicon Cancer Hotspot panel, 47 gene), or NextSeq (Agilent SureSelect XT, 592 gene selected based on COSMIC database) can be used to identify an HR mutation. The sample can be a biological sample or a biopsy sample (e.g., a paraffin-embedded biopsy sample) from the patient. In some embodiments, the patient is a patient suspected of having a cancer having a mutation in a HR-associated gene (e.g., BRCA1/2 mutation in breast or ovarian cancer).

Exemplary methods for determining POLQ overexpressing cancers are described, e.g., in EP 2710142, which is incorporated herein by reference in its entirety. Exemplary methods to identify a BRC A mutation in cancer are described, for example, in WO1998043092 and WO 2013124740, both of which are incorporated herein by reference.

Cancers

Suitable Examples of cancers known to have mutations in HR-associated genes (and are, thus, HR-deficient cancers) include gynecologic cancer (e.g., ovarian cancer, breast cancer, fallopian tube cancer, uterine leiomyoma), prostate cancer, non-Hodgkin's lymphoma, colon cancer, lipoma, basal cell skin carcinoma, squamous cell skin carcinoma, osteosarcoma, acute myelogenous leukemia (AML), and other cancers (See, e.g., Helleday (2010) Carcinogenesis vol. 21, no. 6, pp 955-960; D'Andrea AD. Susceptibility pathways in Fanconi's anemia and breast cancer. 2010 N Engl J Med. 362: 1909-1919).

Genetic susceptibility to breast cancer has been linked to mutations of the BRCA1 and BRCA2 genes. It is postulated that a mutation causes a disruption in the protein which causes chromosomal instability in BRCA deficient cells thereby predisposing them to neoplastic transformation. Inherited mutations in the BRCA1 and BRCA2 genes account for approximately 7-10% of all breast cancer cases. Women with BRCA mutations have a lifetime risk of breast cancer between 56-87%, and a lifetime risk of ovarian cancer between 27-44%.

In some embodiments, the present disclosure provides a method of treating breast cancer (e.g., HR-deficient and/or POLQ overexpressing breast cancer). Suitable examples of breast cancer include lobular carcinoma in situ (LCIS), a ductal carcinoma in situ (DCIS), an invasive ductal carcinoma (IDC), inflammatory breast cancer, Paget disease of the nipple, Phyllodes tumor, Angiosarcoma, adenoid cystic carcinoma, low-grade adenosquamous carcinoma, medullary carcinoma, mucinous carcinoma, papillary carcinoma, tubular carcinoma, metaplastic carcinoma, micropapillary carcinoma, mixed carcinoma, or another breast cancer, including triple negative (TNBC), HER positive, neoadjuvant HER2 negative, estrogen receptor positive, progesterone receptor positive, HER and estrogen receptor positive, HER and progesterone receptor positive, estrogen and progesterone receptor positive, and HER and estrogen and progesterone receptor positive.

Epithelial ovarian cancer (EOC) is the most lethal gynecologic malignancy and the fifth most lethal cancer type overall in women in the United States (Siegel et al., 2017, CA Cancer J Clin 67, 7-30). Ovarian cancers often present genome instability (Cancer Genome Atlas Research, 2011), with almost half of the ovarian cancers harbor defects in one or more DNA repair pathways, mostly in HR (Bast et al., 2009, Nature reviews Cancer 9, 415-428; Pal et al., 2005, Cancer 104, 2807-2816). Ovarian cancer cells are initially sensitive to chemotherapeutic drugs such as platinum analogues (carboplatin or cisplatin) but become resistant to these drugs over time (Pignata et al., 2011, Cancer letters 303, 73-83). The extract mechanism of this acquired resistance remains unclear but appears to be multifactorial, including enhanced DNA repair (Shen et al., 2012, Pharmacol Rev 64, 706-721). Therefore, inhibition of the enhanced DNA repair pathway can re-sensitize ovarian cancer cells to platinum analogues.

In some embodiments, the present disclosure provides a method of treating ovarian cancer (e.g., HR-deficient and/or POLQ overexpressing ovarian cancer). Suitable examples of ovarian cancer include epithelial ovarian carcinomas (EOC), maturing teratomas, dysgerminomas, endodermal sinus tumors, granulosa-theca tumors, Sertoli-Leydig cell tumors, primary peritoneal carcinomas, small cell carcinoma of the ovary (SCCO), teratomas of the ovary, sex cord-stromal ovarian cancer, dysgerminoma ovarian germ cell cancer, choriocarcinomas, carcinosarcomas, adenosarcomas, leiomyosarcomas, fibrosarcomas, and Krukenberg tumor.

In some embodiments, the present disclosure provides a method of treating pancreatic cancer (e.g., HR-deficient and/or POLQ overexpressing pancreatic cancer). Suitable examples of pancreatic cancer include tumors affecting the exocrine gland, exocrine tumors, endocrine tumors, islet cell tumors, neuroendocrine tumors, cystic tumours, cancer of the acinar cells, insulinomas, somatostatinomas, gastrinomas, glucagonomas, adenocarcinoma of the pancreas, pancreatoblastoma, sarcomas of the pancreas, adenosquamous carcinomas, colloid carcinomas, hepatoid carcinomas, intraductal papillary mucinous neoplasms, mucinous cystic neoplasms, pancreatic intraepithelial neoplasia, pancreatoblastomas, serous cystadenomas, signet ring cell carcinoma, solid-pseudopapillary neoplasm, and undifferentiated carcinoma with osteoclast-like giant cells.

In some embodiments, the present disclosure provides a method of treating prostate cancer (e.g., HR-deficient and/or POLQ overexpressing prostate cancer). Suitable examples of prostate cancer include prostate adenocarcinoma, acinar adenocarcinoma, ductal adenocarcinoma, transitional cell (or urothelial) cancer, squamous cell cancer, small cell prostate cancer, carcinoid, sarcomas, small cell carcinomas, neuroendocrine tumors, and transitional cell carcinomas. In some embodiments, the prostate cancer is advanced prostate cancer with germane to somatic homologous recombination deficiency.

Additional examples of cancers that can be treated using the methods described herein include lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastroesophageal cancer, gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma, hepatobiliary cancer); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CIVIL), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasmlungrectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva). In some embodiments, the cancer is ovarian cancer, bladder cancer, breast cancer, endometrial cancer, prostate cancer or pancreatic cancer.

HR-deficient cells (e.g., BRCA1/2 deficient cells) are hypersensitive to PARP inhibition, since PARP inactivation prevents the repair of DNA single-strand breaks (SSBs), which are subsequently converted to double-strand breaks (DSBs) (Brody, 2005, the New England journal of medicine 353, 949-950; Farmer et al., 2005, Nature 434, 917-921; McCabe et al., 2006, Cancer research 66, 8109-8115). Loss of HR accounts for the genomic instability of cancer cells and for their cellular hyper-dependence on alternative poly-ADP ribose polymerase (PARP)-mediated DNA repair mechanisms. PARP expression and activity are significantly up-regulated in certain cancers, suggesting that these cancer cells can rely more than normal cells on the activity of PARP. Thus, agents that inhibit the activity of PARP or reduce the expression level of PARP, collectively referred to herein as "PARP inhibitors (PARPi)", can be useful cancer therapeutics. Suitable examples of PARPi include iniparib (BSI 201), talazoparib (BMN-673), niraparib, olaparib (AZD-2281, TOPARP-A), rucaparib (AG014699, PF-01367338), veliparib (ABT-888), CEP 9722, MK 4827, BGB-290 and 3-aminobenzamide, 4-amino-L8-naphthalimide, benzamide, BGP-15, BYK204165, 3,4-Dihydro-5-[4-(1-piperidinyl)butoxyl]-1(2H)-isoquinolinone, DR2313, 1,5-Isoquinolinediol, MC2050, ME0328, PJ-34 hydrochloride hydrate, and UPF-1069. As used herein, the term "PARP" includes at least PARP1 and PARP2. PARP1 is the founding member of a large family of poly(ADP-ribose) polymerases with 17 members identified (Ame et ah, Bioessays 26:882-893, 2004). It is the primary enzyme catalyzing the transfer of ADP-ribose units from NAD+ to target proteins including PARP1 itself. Under normal physiologic conditions, PARP1 facilitates the repair of DNA base lesions by helping recruit base excision repair proteins XRCC1 and Poïβ (Dantzer et ah, Methods Enzymol. 409:493-510, 2006).

In some embodiments, any of the cancers described herein is PARP inhibitor-resistant. POLQ channels HR repair by antagonizing HR and promoting PARP-dependent error-prone repair. Without wishing to be bound by any particular theory, it is believed that inhibition of POLQ is expected to enhance cell death of PARP inhibitor-resistant cancers. For instance, the PARP enzyme cooperates with POLQ in the process of Alternative End-Joining Repair (Alt-EJ). PARP is required to localize POLQ at the site of the double strand break (DSB) repair. Human tumors can become resistant to PARP inhibitors; however, these tumors can still be sensitive to a POLQ inhibitor if POLQ can localize to the DSB in a PARP-independent manner. Accordingly, aspects of the disclosure provide methods for treating a cancer that is resistant to PARP inhibitor therapy. A cancer that is resistant to a PARP inhibitor means that the cancer does not respond to such inhibitor, for example as evidenced by continued proliferation and increasing tumor growth and burden. In some instances, the cancer can have initially responded to treatment with such inhibitor (referred to herein as a previously administered therapy) but can have grown resistant after a time. In some instances, the cancer can have never responded to treatment with such inhibitor at all. Cancers resistant to PARP inhibitors can be identified using methods known in the art (see, e.g., WO 2014205105, U.S. Pat. No. 8,729,048; incorporated herein by reference). Suitable examples of cancers resistant to PARP-inhibitors include breast cancer, ovarian cancer, lung cancer, bladder cancer, liver cancer, head and neck cancer, pancreatic cancer, gastrointestinal cancer, and colorectal cancer.

Compounds of Formula (I)

The present disclosure provides compounds useful in treating cancer (e.g., cancer having alterations in genes regulating homologous recombination (HR) repair). In some embodiments, such compounds include a compound of Formula (I):

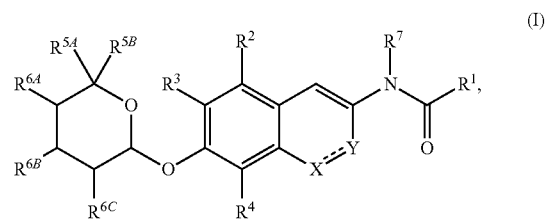

or a pharmaceutically acceptable salt thereof, wherein:
the bond == between X and Y is a single bond or a double bond;
X and Y are independently selected from the group consisting of: O, N, CH, and C(=O);
$R^1$ is selected from the group consisting of: $C_{1-6}$ alkyl, $C_{2-6}$ alkenyl, $C_{2-6}$ alkynyl, $C_{1-4}$ haloalkyl, $C_{6-12}$ aryl and 5-10 membered heteroaryl, each of which is optionally substituted by 1, 2, or 3 groups independently selected from the group consisting of: $Cy^1$ and $R^g$;
$R^2$ and $R^3$ are independently selected from the group consisting of: H, $C_{1-6}$ alkyl, $C_{2-6}$ alkenyl, $C_{2-6}$ alkynyl, $C_{1-4}$ haloalkyl, $C_{1-6}$ alkoxy, and $C_{1-6}$ haloalkoxy;
$R^4$ is selected from the group consisting of: H, $C_{1-6}$ alkyl, $C_{2-6}$ alkenyl, $C_{2-6}$ alkynyl, $C_{1-4}$ haloalkyl, $C_{6-12}$ aryl, and $C_{6-12}$ aryl-$C_{1-3}$ alkylene;
$R^{5A}$ and $R^{5B}$ are independently selected from the group consisting of: H and $C_{1-3}$ alkyl;

$R^{6A}$, $R^{6B}$ and $R^{6C}$ are independently selected from the group consisting of: OH, $C_{1-6}$ alkoxy, $C_{1-6}$ haloalkoxy, $C(=O)NR^{a1}R^{a2}$, and $C(O)OR^{a1}$;

$R^{a1}$ and $R^{a2}$ are independently selected from the group consisting of: H and $C_{1-3}$ alkyl;

$R^7$ is selected from the group consisting of: H, $C_{1-6}$ alkyl, $C_{2-6}$ alkenyl, $C_{2-6}$ alkynyl, and $C_{1-4}$ haloalkyl, each of which is optionally substituted by 1 or 2 $Cy^1$;

each $Cy^1$ is independently selected from the group consisting of: $C_{6-12}$ aryl and 5-10 membered heteroaryl, each of which is optionally substituted by 1, 2, or 3 independently selected $R^g$ groups; and each $R^g$ is independently selected from the group consisting of: OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino and di($C_{1-6}$ alkyl)amino.

In some embodiments, X is N and Y is CH, and the bond === between X and Y is a double bond. In some embodiments, X is CH and Y is N, and the bond === between X and Y is a double bond. In some embodiments, X is O and Y is CH, and the bond === between X and Y is a single bond. In some embodiments, X is CH and Y is O, and the bond === between X and Y is a single bond. In some embodiments, X is O and Y is C(=O), and the bond === between X and Y is a single bond. In some embodiments, X is C(=O) and Y is O, and the bond === between X and Y is a single bond.

In some embodiments, $R^1$ is selected from the group consisting of: $C_{1-6}$ alkyl, $C_{2-6}$ alkenyl, $C_{2-6}$ alkynyl, and $C_{1-4}$ haloalkyl.

In some embodiments, $R^1$ is $C_{6-12}$ aryl, optionally substituted by 1 or 2 groups independently selected from the group consisting of: $Cy^1$ and $R^g$.

In some embodiments, $R^1$ is 5-10 membered heteroaryl, optionally substituted by 1 or 2 groups independently selected from the group consisting of: $Cy^1$ and $R^g$.

In some embodiments, $R^1$ is selected from the group consisting of: $C_{1-6}$ alkyl, $C_{6-12}$ aryl and 5-10 membered heteroaryl, each of which is optionally substituted by 1 or 2 groups independently selected from the group consisting of: $Cy^1$ and $R^g$. In some embodiments, $R^1$ is $C_{1-6}$ alkyl.

In some embodiments, $R^1$ is 5-10 membered heteroaryl.

In some embodiments, $R^1$ is $C_{6-12}$ aryl.

In some embodiments, $R^1$ is selected from the group consisting of: methyl, 3-(3-methylbut-2-en-1-yl)-4-hydroxyphenyl, 3',6-dimethoxy-[1,1'-biphenyl-3-yl], and indol-2-yl.

In some embodiments, $R^2$ and $R^3$ are independently selected from the group consisting of: H, $C_{1-6}$ alkyl, $C_{2-6}$ alkenyl, $C_{2-6}$ alkynyl, and $C_{1-4}$ haloalkyl.

In some embodiments, $R^2$ and $R^3$ are independently selected from the group consisting of: H, $C_{1-6}$ alkoxy, and $C_{1-6}$ haloalkoxy.

In some embodiments, $R^2$ and $R^3$ are independently selected from the group consisting of: H and $C_{1-6}$ alkoxy.

In some embodiments, $R^2$ is H, and $R^3$ is selected from the group consisting of: $C_{1-6}$ alkyl, $C_{2-6}$ alkenyl, $C_{2-6}$ alkynyl, $C_{1-4}$ haloalkyl, $C_{1-6}$ alkoxy, and $C_{1-6}$ haloalkoxy.

In some embodiments, $R^2$ is H, and $R^3$ is selected from the group consisting of: $C_{1-6}$ alkyl, $C_{1-4}$ haloalkyl, $C_{1-6}$ alkoxy, and $C_{1-6}$ haloalkoxy.

In some embodiments, $R^2$ and $R^3$ are each H.

In some embodiments, $R^2$ is H and $R^3$ is $C_{1-6}$ alkoxy.

In some embodiments, $R^2$ is $C_{1-6}$ alkoxy and $R^3$ is H.

In some embodiments, $R^2$ and $R^3$ are independently selected from the group consisting of: H, methoxy, propoxy, and isopropoxy.

In some embodiments, $R^2$ is H, and $R^3$ is methoxy, propoxy, or isopropoxy.

In some embodiments, $R^3$ is H, and $R^2$ is methoxy, propoxy, or isopropoxy.

In some embodiments, $R^4$ is selected from the group consisting of: H, $C_{1-6}$ alkyl, $C_{6-12}$ aryl, and $C_{6-12}$ aryl-$C_{1-3}$ alkylene. In some embodiments, $R^4$ is H. In some embodiments, $R^4$ is $C_{1-6}$ alkyl. In some embodiments, $R^4$ is $C_{6-12}$ aryl or $C_{6-12}$ aryl-$C_{1-3}$ alkylene.

In some embodiments, $R^4$ is selected from the group consisting of: H, methyl, ethyl, phenyl, and benzyl.

In some embodiments, $R^{5A}$ is H, and $R^{5B}$ is $C_{1-3}$ alkyl (e.g., methyl, ethyl, or n-propyl).

In some embodiments, $R^{5A}$ is $C_{1-3}$ alkyl (e.g., methyl, ethyl, or n-propyl), and $R^{5B}$ is H.

In some embodiments, $R^{5A}$ and $R^{5B}$ are each $C_{1-3}$ alkyl.

In some embodiments, $R^{5A}$ is methyl, and $R^{5B}$ is ethyl, n-propyl, or isopropyl.

In some embodiments, $R^{5A}$ and $R^{5B}$ are each methyl.

In some embodiments, $R^{5A}$ and $R^{5B}$ are each ethyl, n-propyl, or isopropyl.

In some embodiments, $R^{6A}$, $R^{6B}$ and $R^{6C}$ are independently selected from the group consisting of: OH, $C_{1-6}$ alkoxy, $C_{1-6}$ haloalkoxy, and $C(=O)NR^{a1}R^{a2}$.

In some embodiments, $R^{6A}$, $R^{6B}$ and $R^{6C}$ are independently selected from the group consisting of: OH, $C_{1-6}$ alkoxy, and $C(=O)NR^{a1}R^{a2}$.

In some embodiments, $R^{6A}$, $R^{6B}$ and $R^{6C}$ are each $C_{1-6}$ alkoxy.

In some embodiments, $R^{6A}$ is OH or $C_{1-6}$ alkoxy. In some aspects of these embodiments, $R^{6A}$ is OH. In other aspects of these embodiments, $R^{6A}$ is $C_{1-6}$ alkoxy (e.g., methoxy, ethoxy, n-propoxy, or isopropoxy).

In some embodiments, $R^{6B}$ is selected from the group selected from: OH and $C(=O)NR^{a1}R^{a2}$. In some aspects of these embodiments, $R^{6B}$ is selected from the group selected from: OH and $C(=O)NH_2$. In some embodiments, $R^{6B}$ is OH. In other embodiments, $R^{6B}$ is $C(=O)NH_2$.

In some embodiments, $R^{6C}$ is OH or $C_{1-6}$ alkoxy. In some aspects of these embodiments, $R^{6C}$ is OH. In other aspects of these embodiments, $R^{6C}$ is $C_{1-6}$ alkoxy (e.g., methoxy, ethoxy, n-propoxy, or isopropoxy).

In some embodiments, $R^{6A}$ is $C_{1-6}$ alkoxy, $R^{6B}$ is OH or $C(=O)NH_2$, and $R^{6C}$ is OH. In some aspects of these embodiments, $R^{5A}$ and $R^{5B}$ are each $C_{1-3}$ alkyl.

In some embodiments, $R^{5A}$ and $R^{5B}$ are each methyl, $R^{6A}$ is methoxy, $R^{6B}$ is OH or $C(=O)NH_2$, and $R^{6C}$ is OH.

In some embodiments, $R^7$ is selected from the group consisting of: H and $C_{1-6}$ alkyl, wherein the $C_{1-6}$ alkyl is optionally substituted with $Cy^1$.

In some embodiments, $R^7$ is H. In some embodiments, $R^7$ is $C_{1-6}$ alkyl is substituted with $Cy^1$. In some embodiments, $R^7$ is selected from the group consisting of: H and 4-methoxybenzyl.

In some embodiments, $Cy^1$ is $C_{6-12}$ aryl, optionally substituted by 1 or 2 independently selected $R^g$ groups. In some aspects of these embodiments, $Cy^1$ is phenyl, optionally substituted with $R^g$. In some embodiments, $Cy^1$ is selected from the group consisting of: 3-methoxyphenyl and 4-methoxyphenyl.

In some embodiments, $R^g$ is selected from the group consisting of: OH, $C_{2-6}$ alkenyl, and $C_{1-6}$ alkoxy. In some embodiments, $R^g$ is OH. In some embodiments, $R^g$ is $C_{1-6}$ alkoxy. In some embodiments, $R^g$ is selected from the group consisting of: OH, 3-methylbut-2-en-1-yl, and methoxy.

In some embodiments:

$R^1$ is selected from the group consisting of: $C_{1-6}$ alkyl, $C_{6-12}$ aryl and 5-10 membered heteroaryl, each of which is optionally substituted by 1 or 2 groups independently selected from the group consisting of: $Cy^1$ and $R^g$;

$R^2$ and $R^3$ are independently selected from the group consisting of: H and $C_{1-6}$ alkoxy;

$R^4$ is selected from the group consisting of: H, $C_{1-6}$ alkyl, $C_{6-12}$ aryl, and $C_{6-12}$ aryl-$C_{1-3}$ alkylene;

$R^{5A}$ and $R^{5B}$ are each $C_{1-3}$ alkyl;

$R^{6A}$, $R^{6B}$ and $R^{6C}$ are independently selected from the group consisting of: OH, $C_{1-6}$ alkoxy, and $C(=O)NR^{a1}R^{a2}$;

$R^7$ is selected from the group consisting of: H and $C_{1-6}$ alkyl, wherein the $C_{1-6}$ alkyl is optionally substituted with $Cy^1$;

$Cy^1$ is $C_{6-12}$ aryl, optionally substituted by 1 or 2 independently selected $R^g$ groups; and $R^g$ is selected from the group consisting of: OH, $C_{2-6}$ alkenyl, and $C_{1-6}$ alkoxy.

In some embodiments:

$R^1$ is selected from the group consisting of: methyl, indol-2-yl, and phenyl, wherein the phenyl is optionally substituted by 1 or 2 groups independently selected from the group consisting of: $Cy^1$ and $R^g$;

$R^2$ and $R^3$ are independently selected from the group consisting of: H, methoxy, propoxy, and isopropoxy;

$R^4$ is selected from the group consisting of: H, methyl, ethyl, phenyl, and benzyl;

$R^{5A}$ and $R^{5B}$ are each methyl;

$R^{6A}$ is $C_{1-6}$ alkoxy;

$R^{6B}$ is selected from the group selected from: OH and $C(=O)NH_2$;

$R^{6C}$ is OH;

$R^7$ is selected from the group consisting of: H and $C_{1-6}$ alkyl substituted with $Cy^1$;

$Cy^1$ is phenyl, optionally substituted with $R^g$; and $R^g$ is selected from the group consisting of: OH, 3-methylbut-2-en-1-yl, and methoxy.

In some embodiments, the compound of Formula (I) has Formula (A):

or a pharmaceutically acceptable salt thereof.

In some embodiments, the compound of Formula (I) is a compound of Formula (Ia):

or a pharmaceutically acceptable salt thereof.

In some embodiments, the compound of Formula (Ia) has Formula:

or a pharmaceutically acceptable salt thereof.

In some embodiments, the compound of Formula (I) is a compound of Formula (Ib):

or a pharmaceutically acceptable salt thereof.

In some embodiments, the compound of Formula (Ib) has Formula:

or a pharmaceutically acceptable salt thereof.

In some embodiments, the compound of Formula (I) is a compound of Formula (Ic):

or a pharmaceutically acceptable salt thereof.

In some embodiments, the compound of Formula (Ic) has Formula:

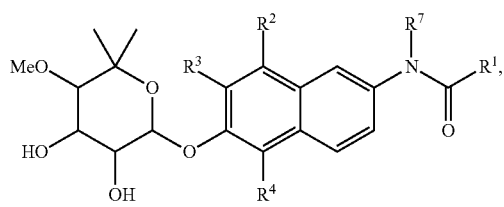
or a pharmaceutically acceptable salt thereof.
In some embodiments, the compound of Formula (I) is selected from the group consisting of:
compound N
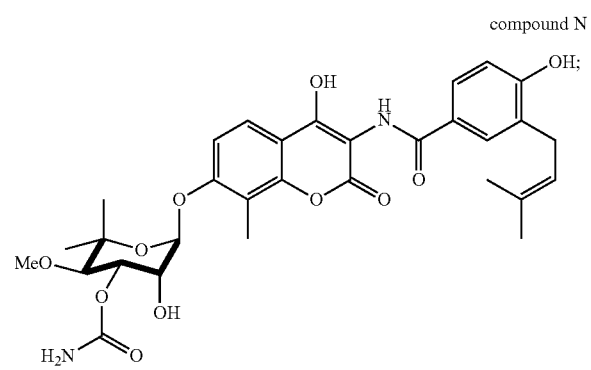
(novobiocin)
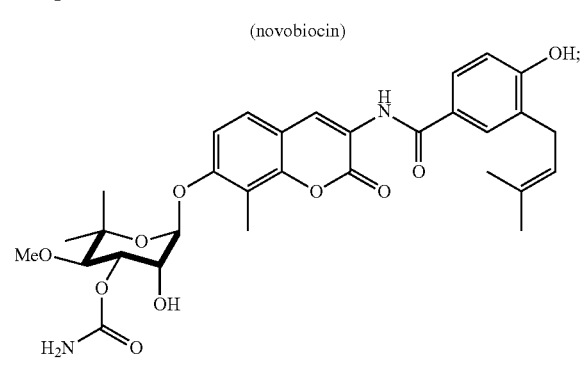
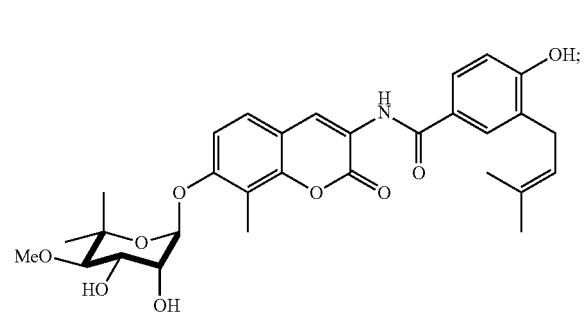
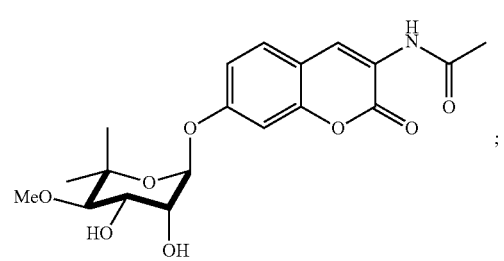
-continued
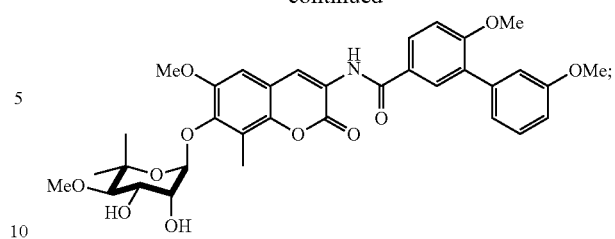
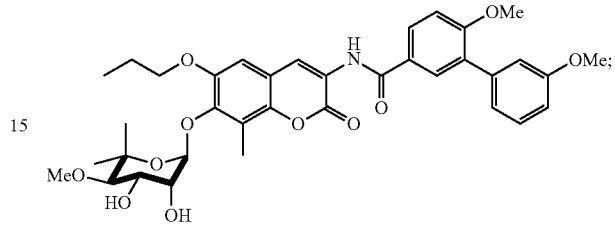
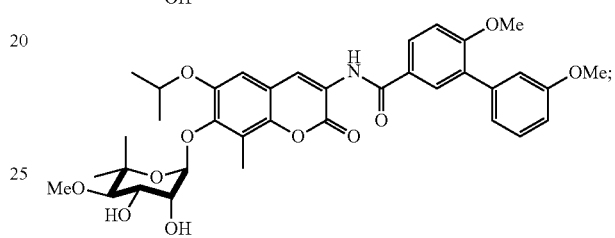
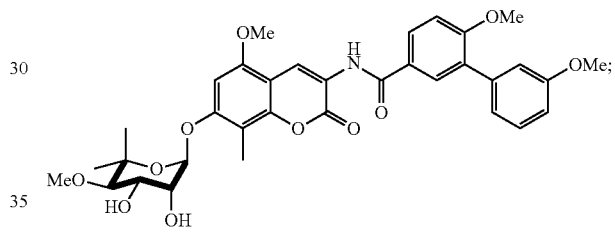
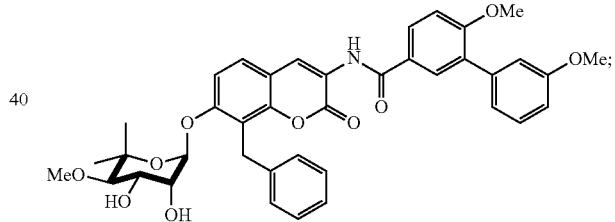
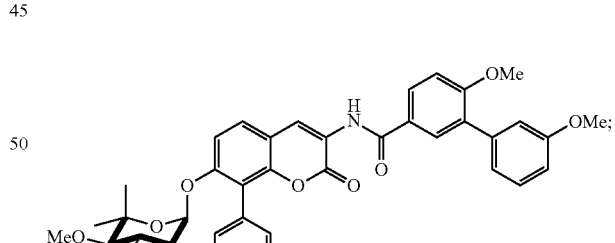
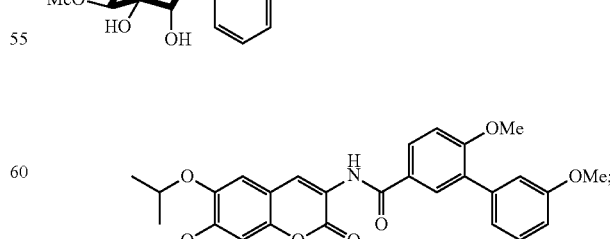
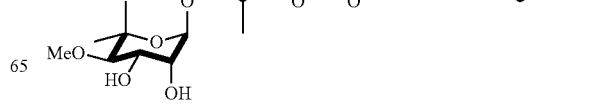

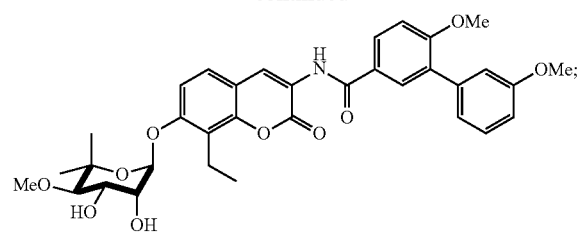
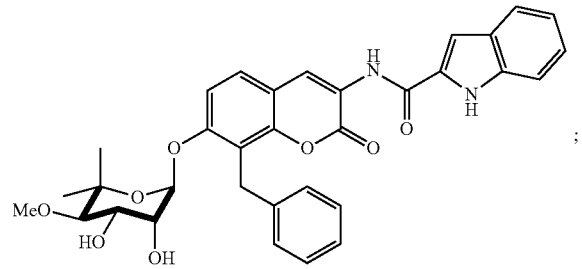
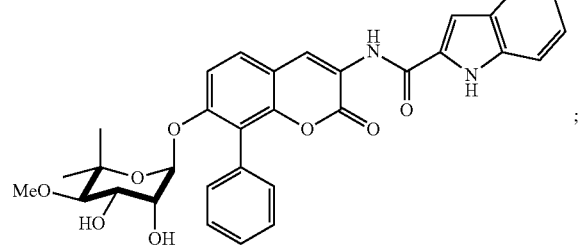
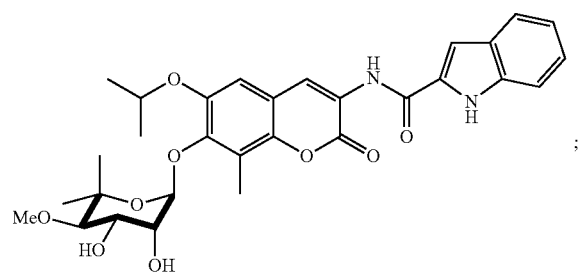
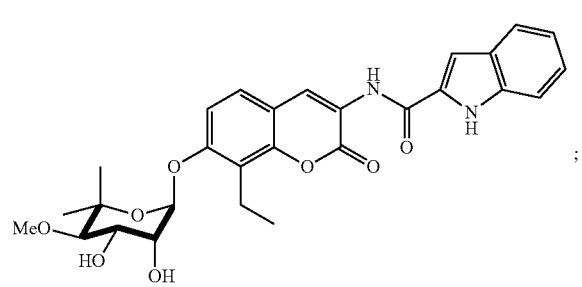
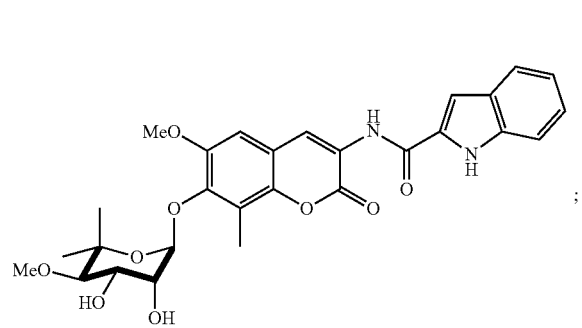
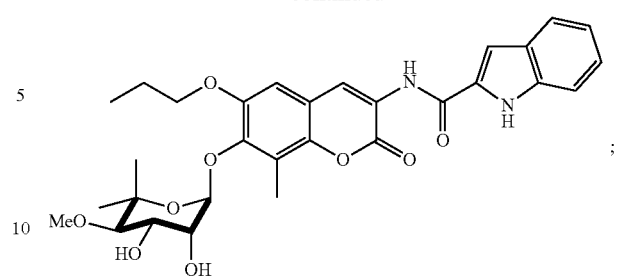
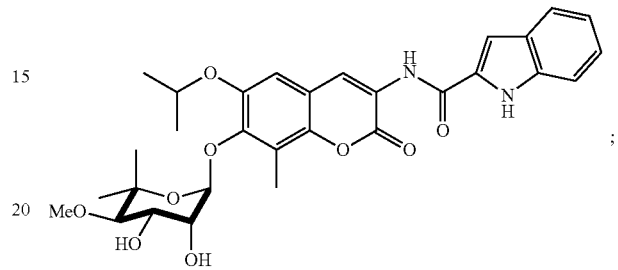
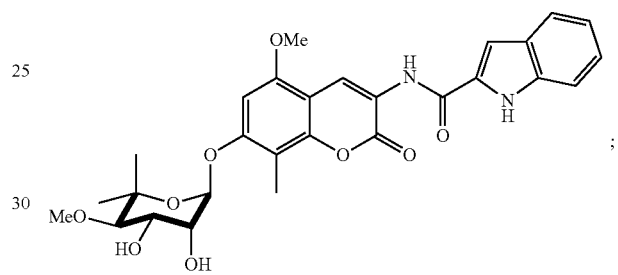
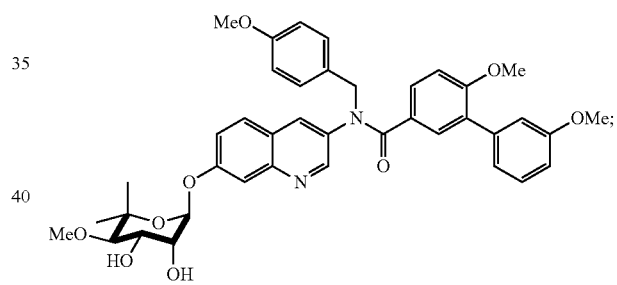
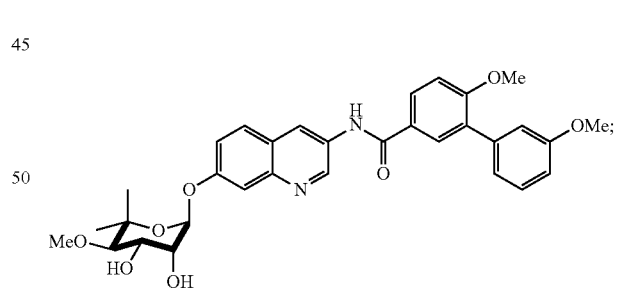
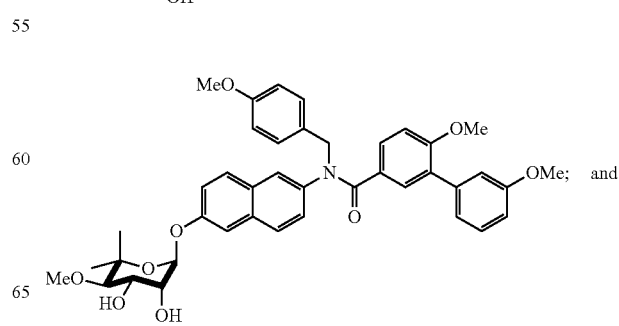

-continued

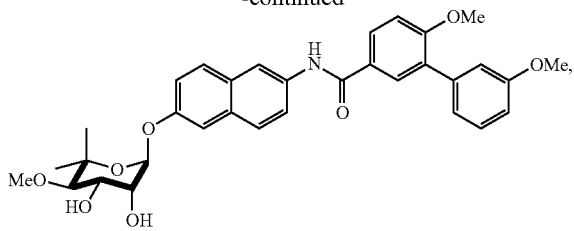

or a pharmaceutically acceptable salt thereof.

Compounds of Formula (I), including salts thereof, can be prepared using known organic synthesis techniques and can be synthesized according to any of numerous possible synthetic routes. For example, the compounds described herein can be prepared using methods and procedures similar to those described in Donnelly, A. et al, The Design, Synthesis, and Evaluation of Coumarin Ring Derivatives of the Novobiocin Scaffold that Exhibit Antiproliferative Activity, *Journal of Organic Chemistry* 2008, 73, 8901-8920, which is incorporated herein by reference in its entirety. A person skilled in the art knows how to select and implement appropriate synthetic protocols, and appreciates that a broad repertoire of synthetic organic reactions is available to be potentially employed in synthesizing compounds provided herein.

Suitable synthetic methods of starting materials, intermediates and products can be identified by reference to the literature, including reference sources such as: Advances in Heterocyclic Chemistry, Vols. 1-107 (Elsevier, 1963-2012); *Journal of Heterocyclic Chemistry* Vols. 1-49 (*Journal of Heterocyclic Chemistry*, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, $4^{th}$ Ed., Wiley & Sons, Inc., New York (2006).

Combination Therapies

The compounds of Formula (I) can be used in combination with anti-cancer therapies (e.g., anti-cancer agents, or therapies such as surgery, transplantation or radiotherapy). These anti-cancer therapies can show a synergistic effect in the treatment of cancers described herein (e.g., HR-deficient cancers, cancers resistant to poly (ADP-ribose) polymerase (PARP) inhibitor therapy, POLQ overexpressing cancer, and/or cancers characterized by one or more BRCA mutations and/or reduced expression of Fanconi (Fane) proteins). As used herein, "synergistic" refers to the joint action of agents (e.g., pharmaceutically active agents), that when taken together increase each other's effectiveness. For example, in some embodiments, in an HR-deficient cancer, POLQ-mediated Alt-EJ in the enhanced pathway. Hence, a POLQ inhibitor can re-sensitize HR-deficient cancer (e.g., ovarian cancer) to a PARP inhibitor or a platinum analogue.

In some embodiments, the anti-cancer therapy is selected from the group consisting of surgery, radiation therapy, chemotherapy, gene therapy, DNA therapy, viral therapy, RNA therapy, adjuvant therapy, and immunotherapy.

In some embodiments, the chemotherapy comprises administering to the subject a cytotoxic agent in an amount effective to treat the HR-deficient cancer. In some embodiments, the cytotoxic agent is selected from the group consisting of a platinum agent, mitomycin C, a poly (ADP-ribose) polymerase (PARP) inhibitor (e.g., any one of PARP inhibitors described herein), a radioisotope, a vinca alkaloid, an antitumor alkylating agent, a monoclonal antibody and an antimetabolite. In some embodiments, the cytotoxic agent is an ataxia telangiectasia mutated (ATM) kinase inhibitor.

Suitable examples of platinum agents include cisplatin, carboplatin, oxaliplatin, satraplatin, picoplatin, nedaplatin, triplatin, and lipoplatin.

Suitable examples of cytotoxic radioisotopes include $^{67}$Cu, $^{67}$Ga, $^{90}$Y, $^{131}$I. $^{177}$Lu, $^{186}$Re, $^{188}$Re, α-Particle emitter, $^{211}$At, $^{213}$Bi, $^{225}$Ac, Auger-electron emitter, $^{125}$I, $^{212}$Pb, and $^{111}$In.

Suitable examples of antitumor alkylating agents include nitrogen mustards, cyclophosphamide, mechlorethamine or mustine (HN2), uramustine or uracil mustard, melphalan, chlorambucil, ifosfamide, bendamustine, nitrosoureas, carmustine, lomustine, streptozocin, alkyl sulfonates, busulfan, thiotepa, procarbazine, altretamine, triazenes, dacarbazine, mitozolomide, and temozolomide.

Suitable examples of anti-cancer monoclonal antibodies include to necitumumab, dinutuximab, nivolumab, blinatumomab, pembrolizumab, ramucirumab, obinutuzumab, ado-trastuzumab emtansine, pertuzumab, brentuximab, ipilimumab, ofatumumab, catumaxomab, bevacizumab, cetuximab, tositumomab-I131, ibritumomab tiuxetan, alemtuzumab, gemtuzumab ozogamicin, trastuzumab, and rituximab.

Suitable examples of vinca alkaloids include vinblastine, vincristine, vindesine, vinorelbine, desoxyvincaminol, vincaminol, vinbumine, vincamajine, vineridine, vinbumine, and vinpocetine.

Suitable examples of antimetabolites include fluorouracil, cladribine, capecitabine, mercaptopurine, pemetrexed, fludarabine, gemcitabine, hydroxyurea, methotrexate, nelarabine, clofarabine, cytarabine, decitabine, pralatrexate, floxuridine, and thioguanine.

In some embodiments, the anti-cancer therapy is an immunotherapy, such as cellular immunotherapy, antibody therapy or cytokine therapy. Without wishing to be bound by any particular theory, POLQ inhibitors are expected to function in many ways similar to PARP inhibitors, and to synergize with immunotherapy. Suitable examples of cellular immunotherapy include dendritic cell therapy and Sipuleucel-T. Suitable examples of antibody therapy include alemtuzumab, ipilimumab, nivolumab, ofatumumab, pembrolizumab, and rituximab. Suitable examples of cytokine therapy include interferons (for example, IFNα, IFNβ, IFNγ, IFNλ) and interleukins. In some embodiments, the immunotherapy comprises one or more immune checkpoint inhibitors. Suitable examples of immune checkpoint proteins include CTLA-4 and its ligands CD80 and CD86, PD-1 with its ligands PD-L1 and PD-L2, and 4-1BB.

Additional examples of anti-cancer therapies include abiraterone acetate (e.g., ZYTIGA), ABVD, ABVE, ABVE-PC, AC, AC-T, ADE, ado-trastuzumab emtansine (e.g., KADCYLA), afatinib dimaleate (e.g., GILOTRIF), aldesleukin (e.g., PROLEUKIN), alemtuzumab (e.g., CAMPATH), anastrozole (e.g., ARIMIDEX), arsenic trioxide (e.g., TRISENOX), asparaginase Erwinia chrysanthemi (e.g., ERWINAZE), axitinib (e.g., INLYTA), azacitidine (e.g., MYLOSAR, VIDAZA), BEACOPP, belinostat (e.g., BELEODAQ), bendamustine hydrochloride (e.g., TREANDA), BEP, bevacizumab (e.g., AVASTIN), bicalutamide (e.g., CASODEX), bleomycin (e.g., BLENOXANE), blinatumomab (e.g., BLINCYTO), bortezomib (e.g., VELCADE), bosutinib (e.g., BOSULIF), brentuximab vedotin (e.g., ADCETRIS), busulfan (e.g., BUSULFEX, MYLERAN), cabazitaxel (e.g., JEVTANA), cabozantinib-s-malate (e.g., COMETRIQ), CAF, capecitabine (e.g., XELODA), CAPDX, carboplatin (e.g., PARAPLAT, PARAPLATIN), carboplatin-taxol, carfilzomib (e.g., KYPROLIS), carmustine (e.g., BECENUM, BICNU, CARMUBRIS), carmustine implant (e.g., GLIADEL WAFER, GLIADEL), ceritinib (e.g., ZYKADIA), cetuximab (e.g., ERBITUX), chlorambucil (e.g., AMBOCHLORIN, AMBOCLORIN, LEUKERAN, LINFOLIZIN), chlorambucil-prednisone, CHOP, cisplatin (e.g., PLATINOL, PLATINOL-AQ), clofarabine (e.g., CLOFAREX, CLOLAR), CMF, COPP, COPP-ABV, crizotinib (e.g., XALKORI), CVP, cyclophosphamide (e.g., CLAFEN, CYTOXAN, NEOSAR), cytarabine (e.g., CYTOSAR-U, TARABINE PFS), dabrafenib (e.g., TAFINLAR), dacarbazine (e.g., DTIC-DOME), dactinomycin (e.g., COSMEGEN), dasatinib (e.g., SPRYCEL), daunorubicin hydrochloride (e.g., CERUBIDINE), decitabine (e.g., DACOGEN), degarelix, denileukin diftitox (e.g., ONTAK), denosumab (e.g., PROLIA, XGEVA), Dinutuximab (e.g., UNITUXIN), docetaxel (e.g., TAXOTERE), doxorubicin hydrochloride (e.g., ADRIAMYCIN PFS, ADRIAMYCIN RDF), doxorubicin hydrochloride liposome (e.g., DOXIL, DOX-SL, EVACET, LIPODOX), enzalutamide (e.g., XTANDI), epirubicin hydrochloride (e.g., ELLENCE), EPOCH, erlotinib hydrochloride (e.g., TARCEVA), etoposide (e.g., TOPOSAR, VEPESID), etoposide phosphate (e.g., ETOPOPHOS), everolimus (e.g., AFINITOR DISPERZ, AFINITOR), exemestane (e.g., AROMASIN), FEC, fludarabine phosphate (e.g., FLUDARA), fluorouracil (e.g., ADRUCIL, EFUDEX, FLUOROPLEX), FOLFIRI, FOLFIRI-BEVACIZUMAB, FOLFIRI-CETUXIMAB, FOLFIRINOX, FOLFOX, FU-LV, fulvestrant (e.g., FASLODEX), gefitinib (e.g., IRESSA), gemcitabine hydrochloride (e.g., GEMZAR), gemcitabine-cisplatin, gemcitabine-oxaliplatin, goserelin acetate (e.g., ZOLADEX), Hyper-CVAD, ibritumomab tiuxetan (e.g., ZEVALIN), ibrutinib (e.g., IMBRUVICA), ICE, idelalisib (e.g., ZYDELIG), ifosfamide (e.g., CYFOS, IFEX, IFOSFAMIDUM), imatinib mesylate (e.g., GLEEVEC), imiquimod (e.g., ALDARA), ipilimumab (e.g., YERVOY), irinotecan hydrochloride (e.g., CAMPTOSAR), ixabepilone (e.g., IXEMPRA), lanreotide acetate (e.g., SOMATULINE DEPOT), lapatinib ditosylate (e.g., TYKERB), lenalidomide (e.g., REVLIMID), lenvatinib (e.g., LENVIMA), letrozole (e.g., FEMARA), leucovorin calcium (e.g., WELLCOVORIN), leuprolide acetate (e.g., LUPRON DEPOT, LUPRON DEPOT-3 MONTH, LUPRON DEPOT-4 MONTH, LUPRON DEPOT-PED, LUPRON, VIADUR), liposomal cytarabine (e.g., DEPOCYT), lomustine (e.g., CEENU), mechlorethamine hydrochloride (e.g., MUSTARGEN), megestrol acetate (e.g., MEGACE), mercaptopurine (e.g., PURINETHOL, PURIXAN), methotrexate (e.g., ABITREXATE, FOLEX PFS, FOLEX, METHOTREXATE LPF, MEXATE, MEXATE-AQ), mitomycin c (e.g., MITOZYTREX, MUTAMYCIN), mitoxantrone hydrochloride, MOPP, nelarabine (e.g., ARRANON), nilotinib (e.g., TASIGNA), nivolumab (e.g., OPDIVO), obinutuzumab (e.g., GAZYVA), OEPA, ofatumumab (e.g., ARZERRA), OFF, olaparib (e.g., LYNPARZA), omacetaxine mepesuccinate (e.g., SYNRIBO), OPPA, oxaliplatin (e.g., ELOXATIN), paclitaxel (e.g., TAXOL), paclitaxel albumin-stabilized nanoparticle formulation (e.g., ABRAXANE), PAD, palbociclib (e.g., IBRANCE), pamidronate disodium (e.g., AREDIA), panitumumab (e.g., VECTIBIX), panobinostat (e.g., FARYDAK), pazopanib hydrochloride (e.g., VOTRIENT), pegaspargase (e.g., ONCASPAR), peginterferon alfa-2b (e.g., PEG-INTRON), peginterferon alfa-2b (e.g., SYLATRON), pembrolizumab (e.g., KEYTRUDA), pemetrexed disodium (e.g., ALIMTA), pertuzumab (e.g., PERJETA), plerixafor (e.g., MOZOBIL), pomalidomide (e.g., POMALYST), ponatinib hydrochloride (e.g., ICLUSIG), pralatrexate (e.g., FOLOTYN), prednisone, procarbazine hydrochloride (e.g., MATULANE), radium 223 dichloride (e.g., XOFIGO), raloxifene hydrochloride (e.g., EVISTA, KEOXIFENE), ramucirumab (e.g., CYRAMZA), R-CHOP, recombinant HPV bivalent vaccine (e.g., CERVARIX), recombinant human papillomavirus (e.g., HPV) nonavalent vaccine (e.g., GARDASIL 9), recombinant human papillomavirus (e.g., HPV) quadrivalent vaccine (e.g., GARDASIL), recombinant interferon alfa-2b (e.g., INTRON A), regorafenib (e.g., STIVARGA), rituximab (e.g., RITUXAN), romidepsin (e.g., ISTODAX), ruxolitinib phosphate (e.g., JAKAFI), siltuximab (e.g., SYLVANT), sipuleucel-t (e.g., PROVENGE), sorafenib tosylate (e.g., NEXAVAR), STANFORD V, sunitinib malate (e.g., SUTENT), TAC, tamoxifen citrate (e.g., NOLVADEX, NOVALDEX), temozolomide (e.g., METHAZOLASTONE, TEMODAR), temsirolimus (e.g., TORISEL), thalidomide (e.g., SYNOVIR, THALOMID), thiotepa, topotecan hydrochloride (e.g., HYCAMTIN), toremifene (e.g., FARESTON), tositumomab and iodine I 131 tositumomab (e.g., BEXXAR), TPF, trametinib (e.g., MEKINIST), trastuzumab (e.g., HERCEPTIN), VAMP, vandetanib (e.g., CAPRELSA), VEIP, vemurafenib (e.g., ZELBORAF), vinblastine sulfate (e.g., VELBAN, VELSAR), vincristine sulfate (e.g., VINCASAR PFS), vincristine sulfate liposome (e.g., MARQIBO), vinorelbine tartrate (e.g., NAVELBINE), vismodegib (e.g., ERIVEDGE), vorinostat (e.g., ZOLINZA), XELIRI, XELOX, ziv-aflibercept (e.g., ZALTRAP), zoledronic acid (e.g., ZOMETA), or a combination thereof. In certain embodiments, the anti-cancer therapy is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors, modulators of protein stability (e.g., proteasome inhibitors), Hsp90 inhibitors, glucocorticoids, all-trans retinoic acids, and other agents that promote differentiation. In certain embodiments, a POLO inhibitor can be independently administered in combination with an anti-cancer therapy including, e.g., surgery, radiation therapy, transplantation (e.g., stem cell transplantation, bone marrow transplantation), immunotherapy, and chemotherapy. In some embodiments, the anti-cancer therapy is a combination of paclitaxel and olaparib, paclitaxel and carboplatin, olaparib and trabectedin, or carboplatin and niraparib. In some embodiments, the anti-cancer therapy includes rucaparib, olaparib, prexasertib or nivolumab.

Pharmaceutical Compositions and Formulations

The present application also provides pharmaceutical compositions comprising an effective amount of a compound of Formula (I) disclosed herein, or a pharmaceutically acceptable salt thereof, and a pharmaceutically acceptable carrier. The pharmaceutical composition can also comprise at least one of any one of the additional therapeutic agents described herein. In certain embodiments, the application also provides pharmaceutical compositions and dosage forms comprising any one the additional therapeutic agents described herein (e.g., in a kit). The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that can be used in the pharmaceutical compositions of the present application include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, poly ethylene-poly oxypropylene-block polymers, polyethylene glycol, and wool fat.

The compositions or dosage forms can contain any one of the compounds and therapeutic agents described herein in the range of 0.005% to 100% with the balance made up from the suitable pharmaceutically acceptable excipients. The contemplated compositions can contain 0.001%-100% of any one of the compounds and therapeutic agents provided herein, in one embodiment 0.1-95%, in another embodiment 75-85%, in a further embodiment 20-80%, wherein the balance can be made up of any pharmaceutically acceptable excipient described herein, or any combination of these excipients.

Routes of Administration and Dosage Forms

The pharmaceutical compositions of the present application include those suitable for any acceptable route of administration. Acceptable routes of administration include, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intramenigeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions and formulations described herein can conveniently be presented in a unit dosage form, e.g., tablets, capsules (e.g., hard or soft gelatin capsules), sustained release capsules, and in liposomes, and can be prepared by any methods well known in the art of pharmacy. See, for example, Remington: The Science and Practice of Pharmacy, Lippincott Williams & Wilkins, Baltimore, Md. (20th ed. 2000). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, any one of the compounds and therapeutic agents disclosed herein are administered orally. Compositions of the present application suitable for oral administration can be presented as discrete units such as capsules, sachets, granules or tablets each containing a predetermined amount (e.g., effective amount) of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which can beneficially increase the rate of compound absorption. In the case of tablets for oral use, carriers that are commonly used include lactose, sucrose, glucose, mannitol, and silicic acid and starches. Other acceptable excipients can include: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents can be added. Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions or infusion solutions which can contain antioxidants, buffers, bacteriostats and solutes which render the formulation isotonic with the blood of the intended recipient; and aqueous and non-aqueous sterile suspensions which can include suspending agents and thickening agents. The formulations can be presented in unit-dose or multi-dose containers, for example, sealed ampules and vials, and can be stored in a freeze dried (lyophilized) condition requiring only the addition of the sterile liquid carrier, for example water for injections, saline (e.g., 0.9% saline solution) or 5% dextrose solution, immediately prior to use. Extemporaneous injection solutions and suspensions can be prepared from sterile powders, granules and tablets. The injection solutions can be in the form, for example, of a sterile injectable aqueous or oleaginous suspension. This suspension can be formulated according to techniques known in the art using suitable dispersing or wetting agents and suspending agents. The sterile injectable preparation can also be a sterile injectable solution or suspension in a non-toxic parenterally-acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant.

The pharmaceutical compositions of the present application can be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include cocoa butter, beeswax, and polyethylene glycols.

The pharmaceutical compositions of the present application can be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J Pharm Pharmacol,* 56:3-17, 2004 and Ilium, L., *Eur J Pharm Sci* 11:1-18, 2000.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of the pharmaceutical compositions of the present application is especially useful when the desired treatment involves areas or organs readily accessible by topical application. In some embodiments, the topical composition comprises a combination of any one of the compounds and therapeutic agents disclosed herein, and one or more additional ingredients, carriers, excipients, or diluents including absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

The compounds and therapeutic agents of the present application can be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polydimethylsiloxane, polycaprolactone, polyethylene glycol, polylactic acid, ethylene vinyl acetate, and mixtures thereof. The coatings can optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides an implantable drug release device impregnated with or containing a compound or a therapeutic agent, or a composition comprising a compound of the present application or a therapeutic agent, such that said compound or therapeutic agent is released from said device and is therapeutically active.

Dosages and Regimens

In the pharmaceutical compositions of the present application, a therapeutic compound is present in an effective amount (e.g., a therapeutically effective amount).

Effective doses can vary, depending on the diseases treated, the severity of the disease, the route of administration, the sex, age and general health condition of the subject, excipient usage, the possibility of co-usage with other therapeutic treatments such as use of other agents and the judgment of the treating physician.

In some embodiments, an effective amount of a therapeutic compound can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; or from about 0.1 mg/kg to about 0.5 mg/kg).

In some embodiments, an effective amount of a therapeutic compound is about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weekly, once every two weeks, once a month). The compounds and compositions described herein can be administered to the subject in any order. A first therapeutic agent, such as a compound of Formula (I), can be administered prior to or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before or after), or concomitantly with the administration of a second therapeutic agent, such as an anti-cancer therapy described herein, to a subject in need of treatment. Thus, the compound of Formula (I), or a composition containing the compound, can be administered separately, sequentially or simultaneously with the second therapeutic agent, such as a chemotherapeutic agent described herein. When the compound of Formula (I), or a pharmaceutically acceptable salt thereof, and a second or third therapeutic agent are administered to the subject simultaneously, the therapeutic agents can be administered in a single dosage form (e.g., tablet, capsule, or a solution for injection or infusion).

Kits

The present disclosure also includes pharmaceutical kits useful, for example, in the treatment of disorders, diseases and conditions referred to herein, which include one or more containers containing a pharmaceutical composition comprising a therapeutically effective amount of a compound of the present disclosure. Such kits can further include, if desired, one or more of various conventional pharmaceutical kit components, such as, for example, containers with one or more pharmaceutically acceptable carriers, additional containers, etc. Instructions, either as inserts or as labels, indicating quantities of the components to be administered, guidelines for administration, and/or guidelines for mixing the components, can also be included in the kit. The kit can optionally include directions to perform a test to determine a mutation (e.g., HR-associated mutation) in a cancer cell, and/or any of the reagents and device(s) to perform such tests. The kit can optionally include directions to perform a test to determine a POLQ overexpression in a cancer cell, and/or any of the reagents and device(s) to perform such tests. The kit can also optionally include an additional therapeutic agent (e.g., PARP inhibitor).

Definitions

As used herein, the term "about" means "approximately" (e.g., plus or minus approximately 10% of the indicated value).

As used herein, the term "compound" as used herein is meant to include all stereoisomers, geometric isomers, tautomers, and isotopes of the structures named or depicted. Compounds herein identified by name or structure as one particular tautomeric form are intended to include other tautomeric forms unless otherwise specified.

The terms "pharmaceutical" and "pharmaceutically acceptable" are employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" of a disease, condition or disorder refers to decreasing the risk of occurrence of the disease, condition or disorder in a subject or group of subjects (e.g., a subject or group of subjects predisposed to or susceptible to the disease, condition or disorder). In some embodiments, preventing a disease, condition or disorder refers to decreasing the possibility of acquiring the disease, condition or disorder and/or its associated symptoms. In some embodiments, preventing a disease, condition or disorder refers to completely or almost completely stopping the disease, condition or disorder from occurring.

As used herein, the term "pharmaceutically acceptable salt" refers to a salt that is formed between an acid and a basic group of the compound, such as an amino functional group, or between a base and an acidic group of the compound, such as a carboxyl functional group. In some embodiments, the compound is a pharmaceutically acceptable acid addition salt. In some embodiments, acids commonly employed to form pharmaceutically acceptable salts of the therapeutic compounds described herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1, 4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the therapeutic compounds described herein include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine;

N-methyl-D-glucamine; morpholine; thiomorpholine; piperidine; pyrrolidine; and amino acids such as arginine, lysine, and the like.

As used herein, "homologous recombination (HR)", refers to the cellular process of genetic recombination in which nucleotide sequences are exchanged between two similar or identical molecules of DNA. It is most widely used for repairing double-stranded breaks in DNA. Two primary models for how homologous recombination repairs double-strand breaks in DNA are the double-strand break repair (DSBR) pathway (sometimes called the double Holliday junction model) and the synthesis-dependent strand annealing (SDSA) pathway (See, e.g., Sung, P; Klein, H (October 2006). "Mechanism of homologous recombination: mediators and helicases take on regulatory functions". Nature Reviews Molecular Cell Biology 7 (10): 739-750, incorporated herein by reference).

As used throughout, the term "subject" or "patient" is intended to include humans and animals that are capable of suffering from or afflicted with a cancer or any disorder involving, directly or indirectly, a cancer. Examples of subjects include mammals, e.g., humans, dogs, cows, horses, pigs, sheep, goats, cats, mice, rabbits, rats, and transgenic non-human animals. In some embodiments, subjects include companion animals, e.g. dogs, cats, rabbits, and rats. In some embodiments, subjects include livestock, e.g., cows, pigs, sheep, goats, and rabbits. In some embodiments, subjects include thoroughbred or show animals, e.g., horses, pigs, cows, and rabbits. In important embodiments, the subject is a human, e.g., a human having, at risk of having, or potentially capable of having cancer. A "subject in need of treatment" is a subject identified as having cancer. In some embodiments, the subject in need of treatment is identified as having a homologous recombination (HR)-deficient cancer, i.e., the subject has been diagnosed by a physician (e.g., using methods well known in the art; see WO 2014/138101, incorporated herein by reference) as having a HR-deficient cancer. The HR status of the cancer can be determined by, for example, a BRCA 1-specific CGH classifier (Evers et al. Trends Pharmacol Sci. 2010 August; 31(8):372-80), an assay that determines the capacity of primary cell cultures to form foci after PARP inhibition (Mukhopadhyay, A. et al. (2010) Clin. Cancer Res. 16, 2344-2351), or determining the methylation status of BRCA1 (and other HR-associated genes) (Evers et al. Trends Pharmacol Sci. 2010 August; 31(8):372-80). In some embodiments, the HR-deficient cancer is resistant to treatment with a poly (ADP-ribose) polymerase (PARP) inhibitor alone (see, for example, Montoni et al. Front Pharmacol. 2013 Feb 27; 4:18). In some embodiments, the subject in need of treatment is a subject identified as having a cancer that is resistant to or at risk of developing resistance to PARP inhibitor therapy using methods well known in the art (see, e.g., WO 2014205105, WO 2015040378, WO 2011153345; incorporated herein by reference). In some embodiments, the PARP inhibitor-resistant cancer is deficient in homologous recombination (i.e., the cancer is characterized by a lack of a functional homologous recombination (HR) DNA repair pathway, and is resistant to PARP inhibitor therapy).

As used herein, "anti-cancer therapy" refers to any agent, composition or medical technique (e.g., surgery, radiation treatment, etc.) useful for the treatment of cancer. For example, an anti-cancer agent can be a small molecule, antibody, peptide or antisense compound. Suitable examples of antisense compounds include interfering RNAs (e.g., dsRNA, siRNA, shRNA, miRNA, and amiRNA) and antisense oligonucleotides (ASO).

The terms "inhibition", "inhibiting", "inhibit," or "inhibitor" refer to the ability of a compound to reduce, slow, halt, and/or prevent activity of a particular biological process in a cell relative to vehicle. In some embodiments, "inhibit", "block", "suppress" or "prevent" means that the activity being inhibited, blocked, suppressed, or prevented is reduced by at least 5%, 10%, 15%, 20%, 25%, 30%, 35%, 40%, 45%, 50%, 55%, 60%, 65%, 70%, 75%, 80%, 85%, 90%, 95%, or 100% as compared to the activity of a control (e.g., activity in the absence of the inhibitor. In some embodiments, "inhibit", "block", "suppress" or "prevent" means that the activity of the target of the inhibitor (e.g. the ATPase activity of POLQ) is reduced by at least 5%, 10%, 15%, 20%, 25%, 30%, 35%, 40%, 45%, 50%, 55%, 60%, 65%, 70%, 75%, 80%, 85%, 90%, 95%, 100% as compared to a control (e.g., the ATPase activity of POLQ in the absence of the inhibitor).

An "effective amount" refers to an amount sufficient to elicit the desired biological response, i.e., treating cancer. As will be appreciated by those of ordinary skill in this art, the effective amount of the compounds described herein can vary depending on such factors as the desired biological endpoint, the pharmacokinetics of the compound, the condition being treated, the mode of administration, and the age and health of the subject, and the guidance of the treating physician. An effective amount includes that amount necessary to slow, reduce, inhibit, ameliorate or reverse one or more symptoms associated with cancer. For example, in the treatment of cancer, such terms can refer to a reduction in the size of the tumor.

As used in the present application, the term "$C_{n-m}$ alkyl", employed alone or in combination with other terms, refers to a saturated hydrocarbon group that can be straight-chain (linear) or branched, having n to m carbons. Suitable examples of alkyl moieties include chemical groups such as methyl, ethyl, n-propyl, isopropyl, n-butyl, tert-butyl, isobutyl, sec-butyl: higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used in the present application, "$C_{n-m}$ alkenyl" refers to an alkyl group having one or more double carbon-carbon bonds and having n to m carbons. Suitable example alkenyl groups include ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" means a straight or branched chain chemical group containing only carbon and hydrogen, containing n to m carbon atoms and containing at least one carbon-carbon triple bond, such as ethynyl, 1-propynyl, 1-butynyl, 2-butynyl, and the like. In various embodiments, alkynyl groups can either be unsubstituted or substituted with one or more substituents. Typically, alkynyl groups will comprise 2 to 9 carbon atoms (for example, 2 to 6 carbon atoms, 2 to 4 carbon atoms, or 2 carbon atoms). The term "$C_{n-m}$ alkynylene" refers to a divalent alkynyl group.

As used in the present application, the term "$C_{n-m}$ alkoxy", employed alone or in combination with other terms, refers to a group of formula —O—$C_{n-m}$ alkyl, win the present application the alkyl group contains n to m carbon atoms. Suitable exemplary alkoxy groups include methoxy, ethoxy, propoxy (for example, n-propoxy and isopropoxy), butoxy (for example, n-butoxy and tert-butoxy), and the like. In some embodiments, the alkoxy group has 1 to 6, 1 to 4, or 1 to 3 carbon atoms.

As used in the present application, "halo" refers to a halogen atom such as F, Cl, Br, or I. In some embodiments, a halo is F, Cl, or Br. In other embodiments, halo is F, Cl, or I. In other embodiments, halo is F, I, or Br.

As used in the present application, the term "$C_{n-m}$ haloalkyl", employed alone or in combination with other terms, refers to an alkyl group having from one halogen atom to 2s+1 halogen atoms which can be the same or different, where "s" is the number of carbon atoms in the alkyl group, win the present application the alkyl group has n to m carbon atoms. In some embodiments, the haloalkyl group is fluorinated only. In some embodiments, the alkyl group has 1 to 6, 1 to 4, or 1 to 3 carbon atoms.

As used in the present application, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used in the present application, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 membered monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms win the present application one or more (for example, 1, 2, or 3) ring atoms are independently selected from N, O, and S. Exemplary five-membered heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms win the present application one or more (for example, 1, 2, or 3) ring atoms are independently selected from N, O, and S. Exemplary six-membered heteroaryls are pyridyl, pyrazinyl, pyrimidinyl, triazinyl and pyridazinyl.

The term "aromatic" refers to a carbocycle or heterocycle having one or more polyunsaturated rings having aromatic character (that is, having (4n+2) delocalized JI (pi) electrons where n is an integer).

The term "n-membered" where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

The term "aryl," employed alone or in combination with other terms, refers to an aromatic hydrocarbon group, which can be monocyclic or polycyclic (for example, having 2, 3 or 4 fused rings). The term "$C_{n-m}$ aryl" refers to an aryl group having from n to m ring carbon atoms. Aryl groups include, for example, phenyl, naphthyl, anthracenyl, phenanthrenyl, indanyl, indenyl and the like. In some embodiments, aryl groups have from 6 to about 20 carbon atoms, from 6 to about 15 carbon atoms, or from 6 to about 10 carbon atoms. In some embodiments, the aryl group is phenyl.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Suitable examples of alkylamino groups include N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di $C_{n-m}$ alkylamino" refers to a group of formula —N(alkyl)$_2$, wherein each alkyl group independently has n to m carbon atoms. In some embodiments, each alkyl group has 1 to 6, 1 to 4, or 1 to 3 carbon atoms. Suitable examples of dialkylamino groups include N,N-methylethylamino, N,N-diethylamino, N,N-propylethylamino, N,N-butylisopropylamino, and the like.

EXAMPLES

Example 1—POLQ Depletion Sensitize HR-Deficient Cells to PARP

Inhibitors and Carboplatin Drugs To test the effect of POLQ depletion on HR-deficient ovarian cell lines, an HR-deficient ovarian tumor cell line, A2780-shFANCD2 cells was generated. These HR-deficient cells, and the parental A2780 cells, were further subjected to shRNA-mediated POLQ depletion, and their survival fraction following exposure to PARPi or platinum analogues was measured. The results show that POLQ depletion reduces the survival of HR-deficient cells treated with PARPi or carboplatin drugs (FIG. 1B). These data shows that inhibition of POLQ can be a good strategy for re-sensitizing PARPi/platinum analogue resistant cells. The combination of POLQ inhibitor and PARPi/carboplatin would be effective in battling PARPi/carboplatin-resistant, HR-defective cells.

FIG. 1 shows that POLQ is overexpressed in HR-deficient ovarian cancers as a compensatory survival mechanism. FIG. 1A shows POLQ expression in different cancer localizations. FIG. 1B shows that knockdown of POLQ in HR-deficient cells (shFANCD2) sensitizes cells to PARP inhibitor. POLQ and/or FANCD2 depleted cells were treated with increasing concentration of PARPi for a 14 days clonogenic survival assay.

Example 2—Novobiocin (NVB) Selectively Kills the BRCA 1-Deficient Tumor Cells

Novobiocin is a well-known antibiotic. It is known to bind to the ATP-binding pocket of DNA gyrase, and it elicits its antibacterial activity by inhibiting ATP hydrolysis. Data shown in FIGS. 2A-2D, 3 and 4 shows that: (1) Novobiocin inhibits the ATPase of POLQ; (2) Novobiocin inhibits the POLQ ATPase more strongly than it inhibits the ATPase activity of SMARCA or CHD1 (two related ATPases); (3) Novobiocin selectively kills BRCA1-deficient tumor cells, compared to an isogenic BRCA1-proficient cell line; (4) Novobiocin selectively kills HR-deficient cells as strongly as PARP inhibitor; and (5) Novobiocin, or a derivative of this compound, can be useful for precision medicine—i.e., for the treatment of HR-deficient human cancers which have acquired PARPi resistance. Or it can be used in combination with PARPi.

Figure 5:
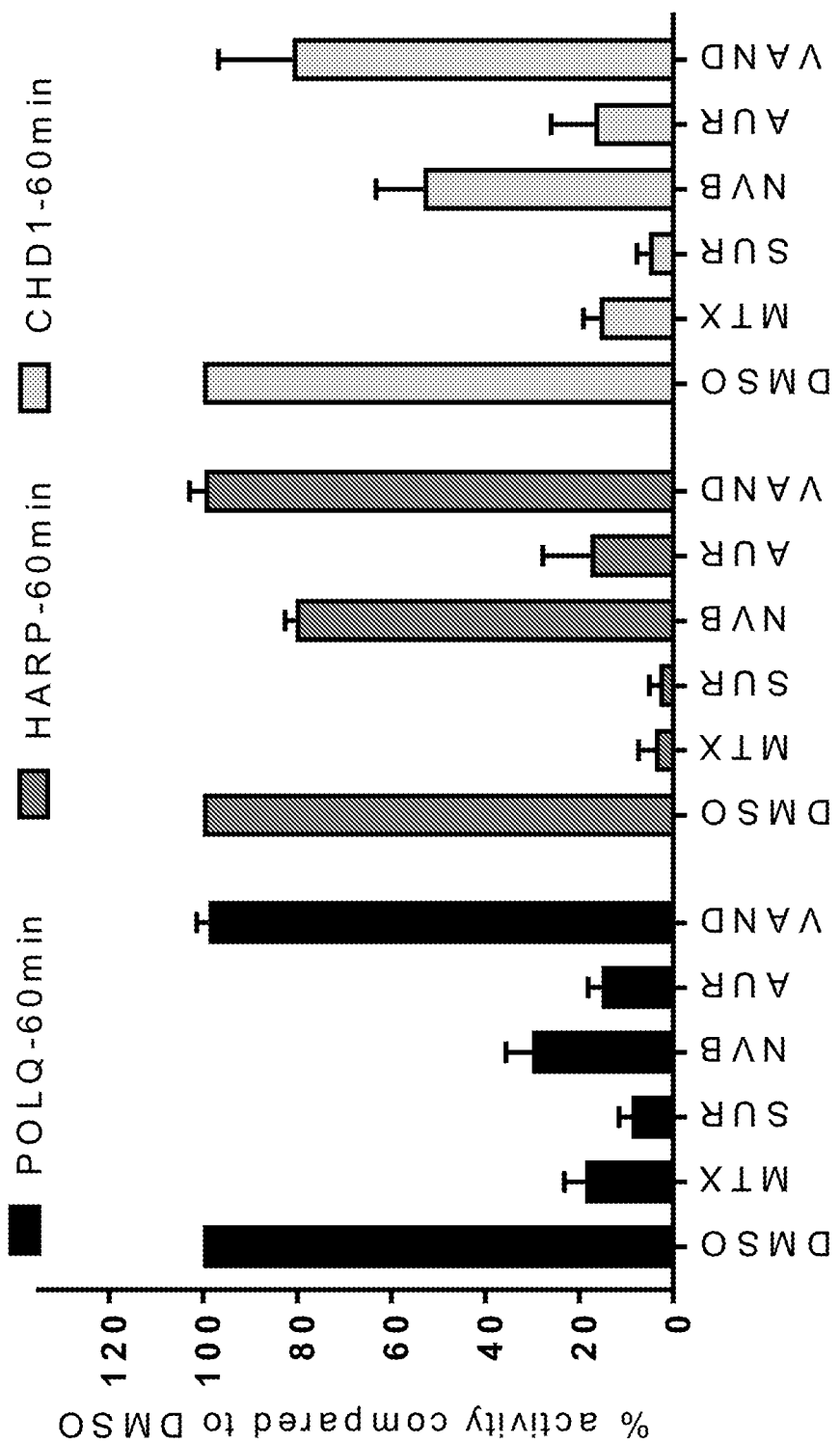
FIG. 5 contains bar graphs showing that novobiocin specifically inhibits ATPase activity of POLQ in a $^{32}$P-based ATPase activity assay.

Data shown in FIG. 5 shows that novobiocin specifically inhibits ATPase activity of POLQ in a $^{32}$P-based ATPase activity assay. 100 µM novobiocin was used in the assay. MTX=Mitoxantrone; SUR=Suramin sodium salt; NVB=novobiocin; AUR=Aurintricarboxylic acid; VAND=vandetanib (EGFR inhibitor, negative control).

Figure 6:
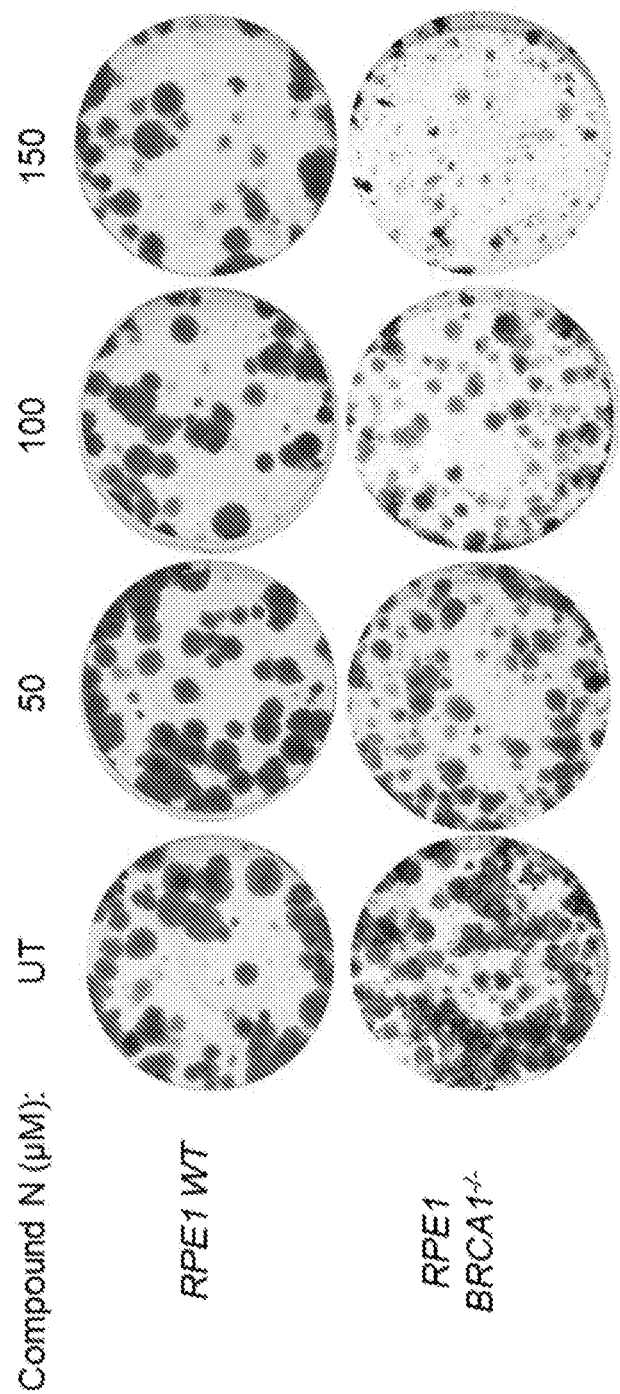
FIG. 6 contains images showing that novobiocin specifically kills BRCA1−/− RPE1 cells in a clonogenic survival assay.
Figure 7:
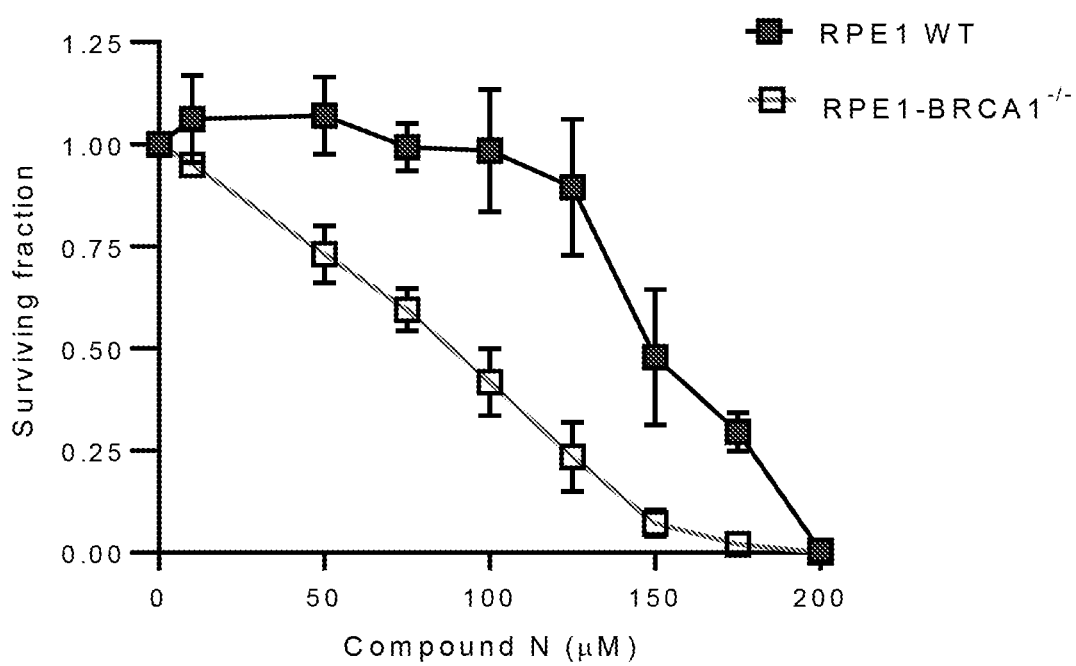
FIG. 7 contains a line plot showing that novobiocin specifically kills BRCA1−/− RPE1 cells in a clonogenic survival assay.

Images shown in FIG. 6 show that novobiocin specifically kills BRCA1-/- RPE1 cells in a clonogenic survival assay. Line plot shown in FIG. 7 shows that novobiocin specifically kills BRCA1-/- RPE1 cells in a clonogenic survival assay.

Figure 8:
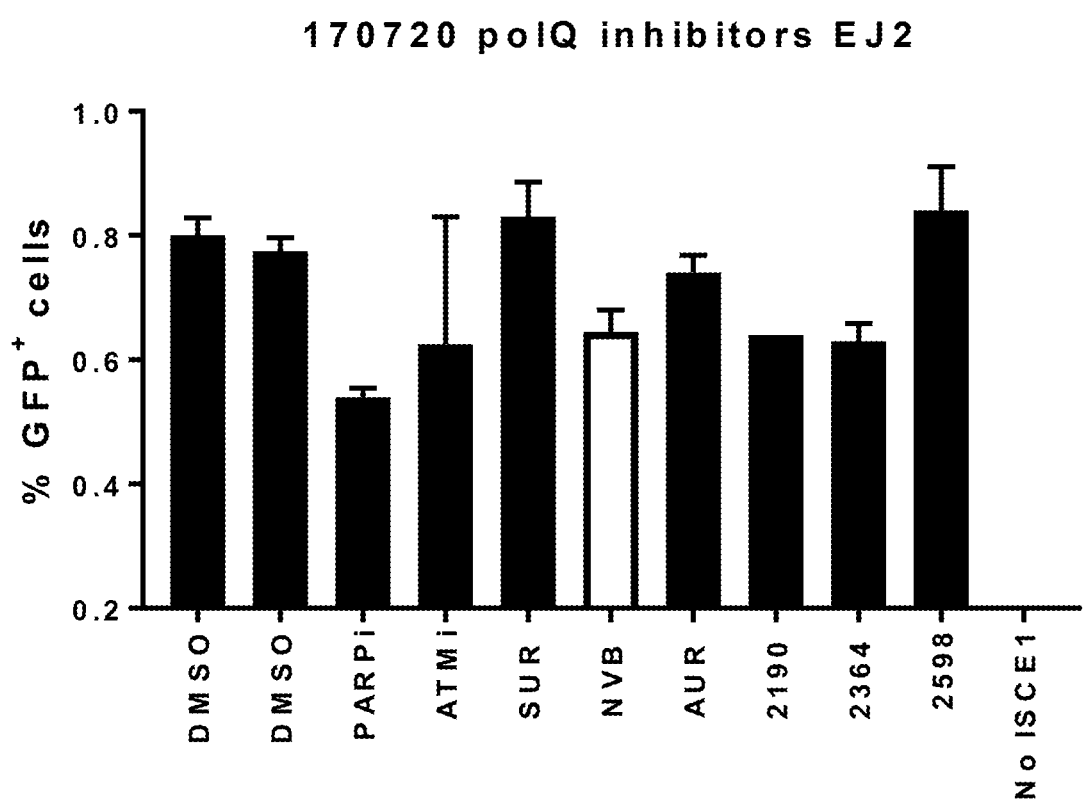
FIG. 8 contains a bar graph showing that novobiocin inhibits alternative end-joining but not homologous recombination at 10 μM.

Bar graph shown in FIG. 8 shows that novobiocin inhibits alternative end-joining but not homologous recombination. 10 µM concentration of each tested compound was used in the assay. Mitoxantrone and VAND kill cells.

Figure 9:
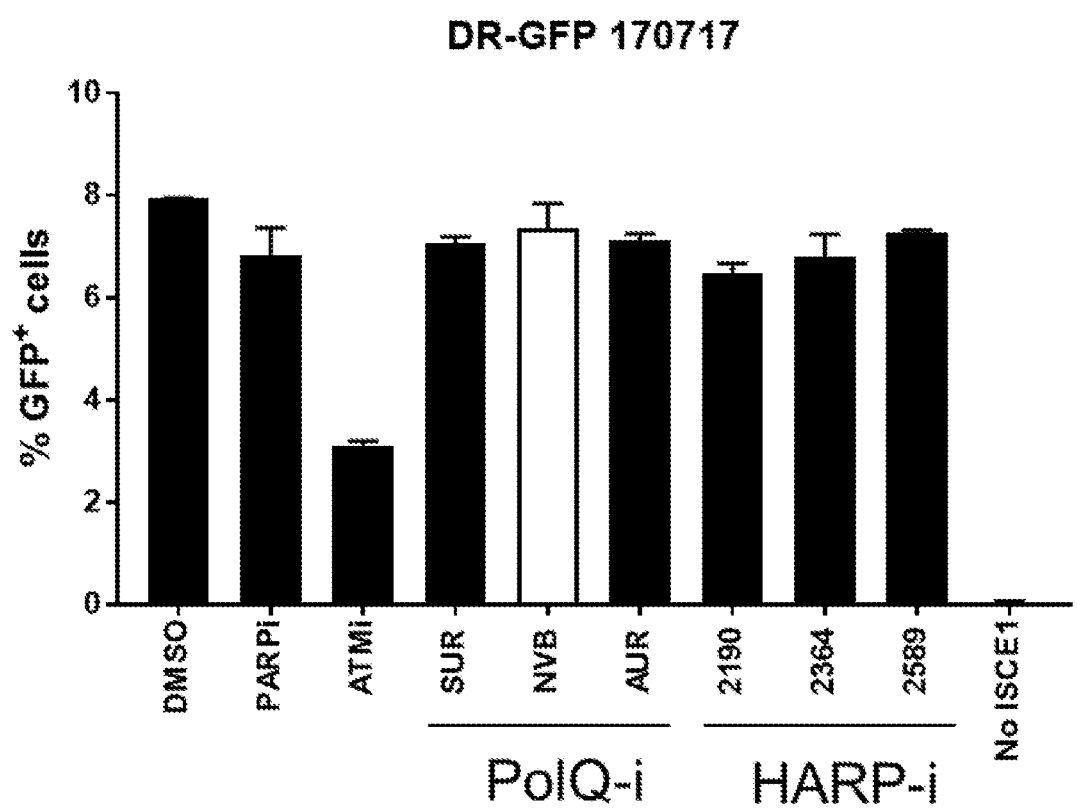
FIG. 9 contains a bar graph showing that novobiocin inhibits alternative end-joining but not homologous recombination at 50 μM.

Bar graph shown in FIG. 9 shows that novobiocin inhibits alternative end-joining but not homologous recombination. 50 µM of each tested compound was used in the assay. Mitoxantrone and VAND killed all cells.

Figure 10:
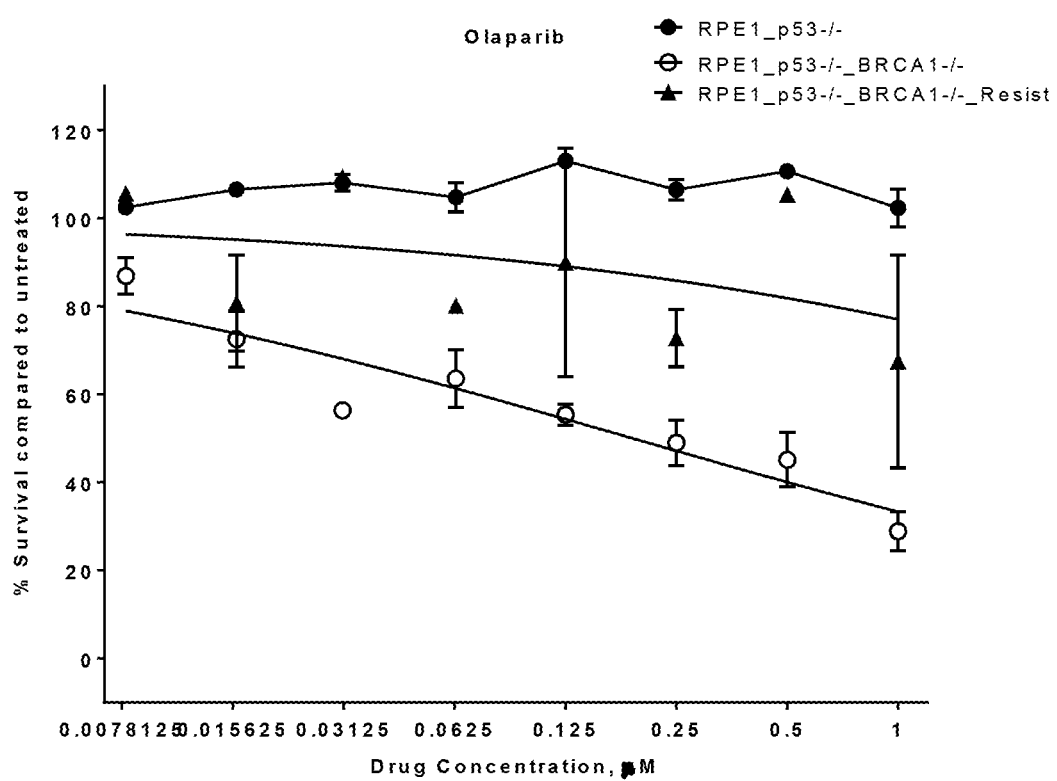
FIG. 10 contains a line plot showing generation of PARP inhibitor (olaparib) resistant cell lines (RPE1 cells).

Line plot shown in FIG. 10 shows generation of PARP inhibitor (olaparib) resistant cell lines (RPE1 cells). Novobiocin kills RPE1 cells that are resistant to the PARP inhibitor.

Figure 11:
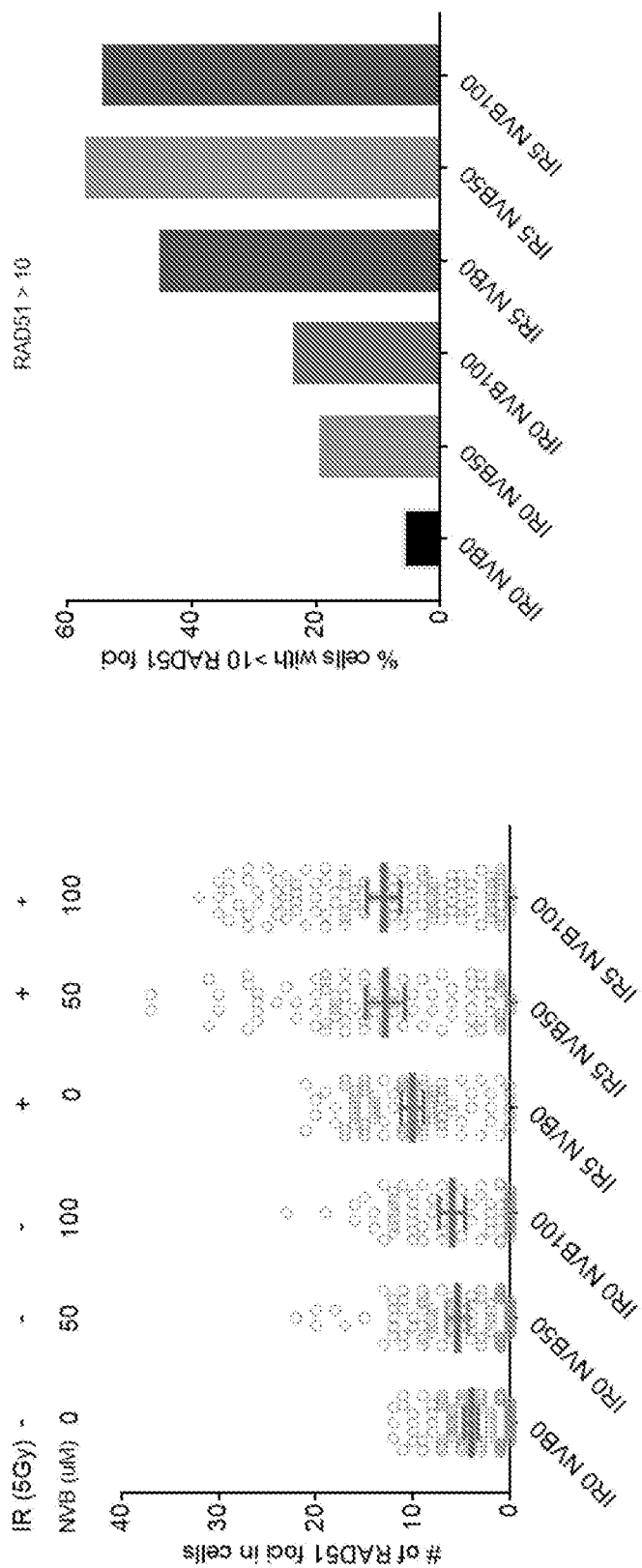
FIG. 11 contains bar graphs showing that novobiocin induces RAD51 foci formation.
Figure 12:
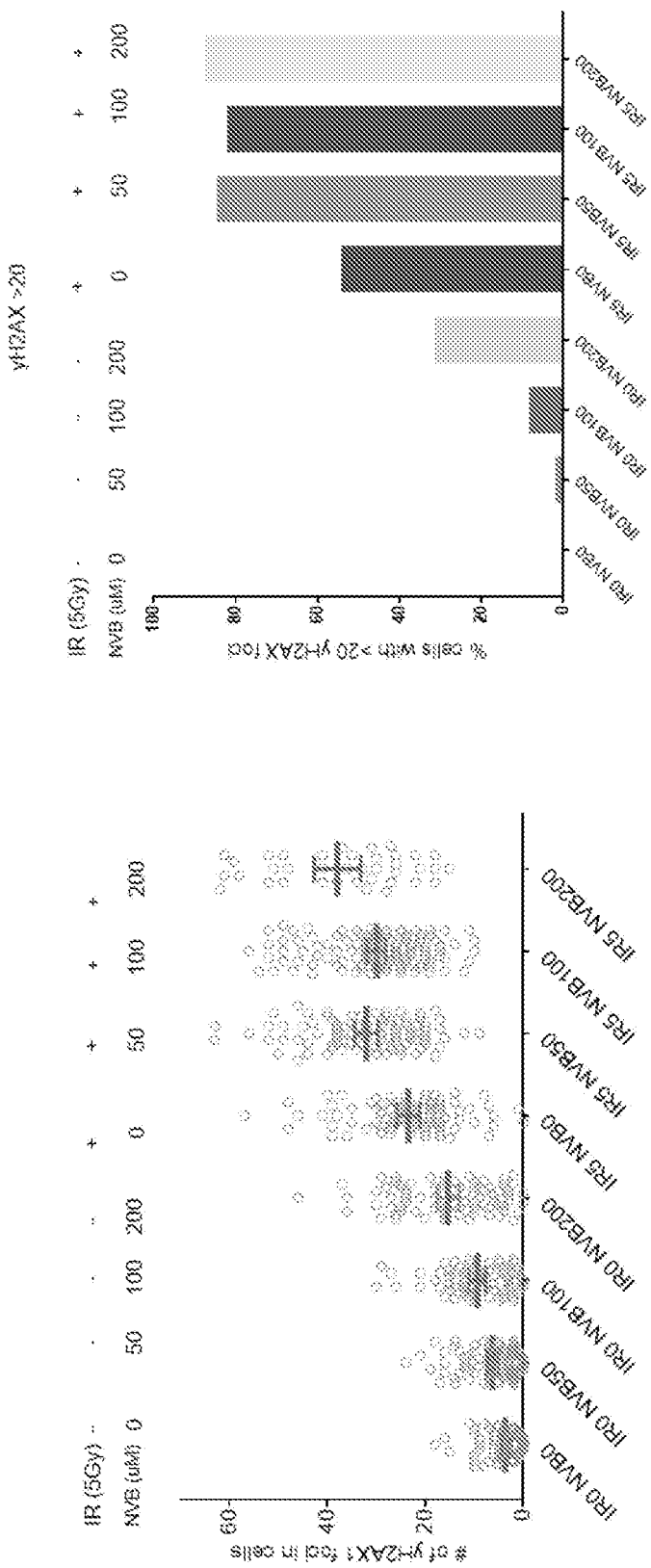
FIG. 12 contains bar graphs showing that novobiocin induces yH2AX foci formation.

Bar graphs shown in FIGS. 11 and 12 show that novobiocin induces RAD51 and yH2AX foci formation.

Figure 13:
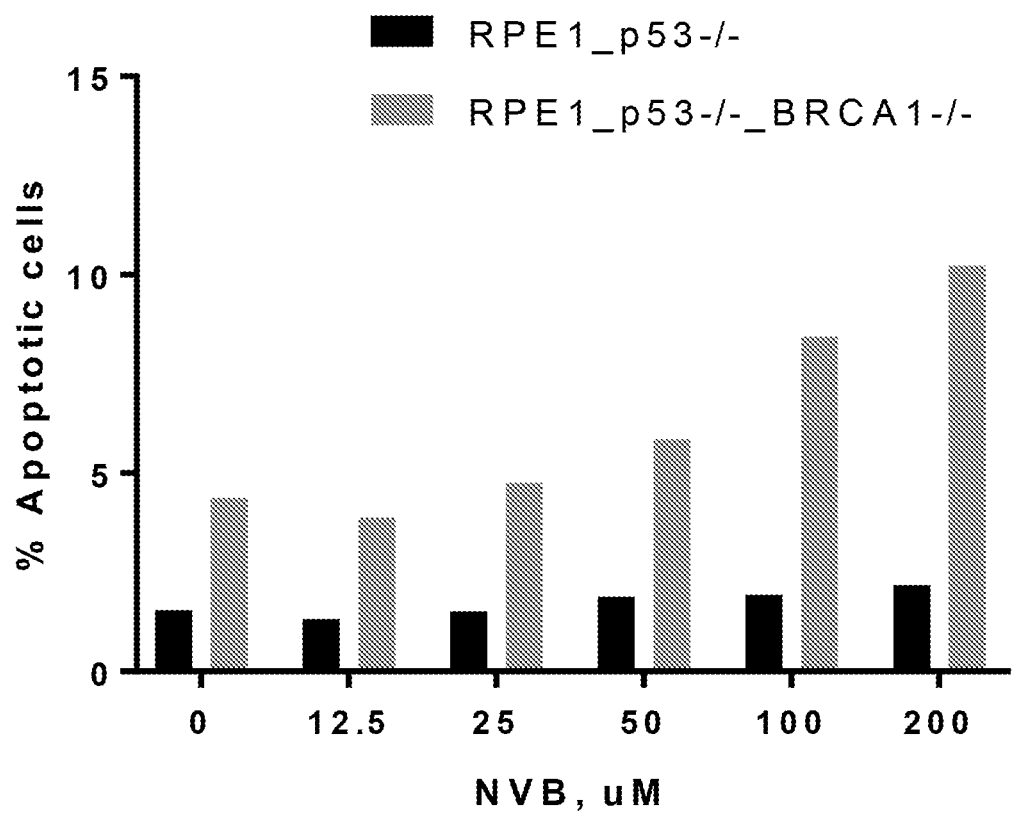
FIG. 13 contains a bar graph showing that novobiocin induces apoptosis specifically in RPE1-p53−/− BRCA1−/− cells.

Bar graph shown in FIG. 13 shows that novobiocin induces apoptosis specifically in RPE1-p53-/- BRCA1-/- cells. Analyzed 4 days after NVB using Annexin V kit.

Figure 14:
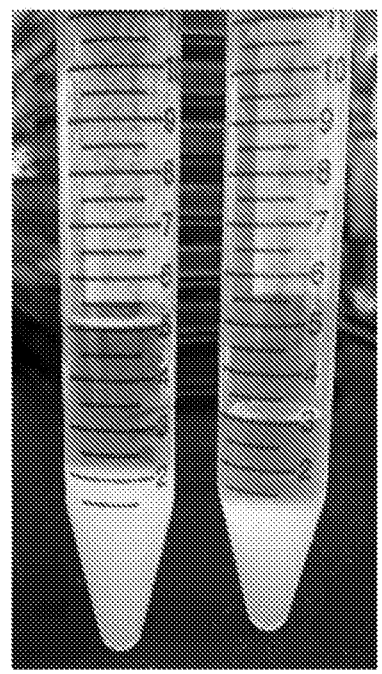
FIG. 14 contains an image showing that novobiocin was successfully conjugated to sepharose beads.

An image shown in FIG. 14 shows that novobiocin was successfully conjugated to sepharose beads. The color in the left tube is attributed to the novobiocin bound to the beads.

Figure 15:
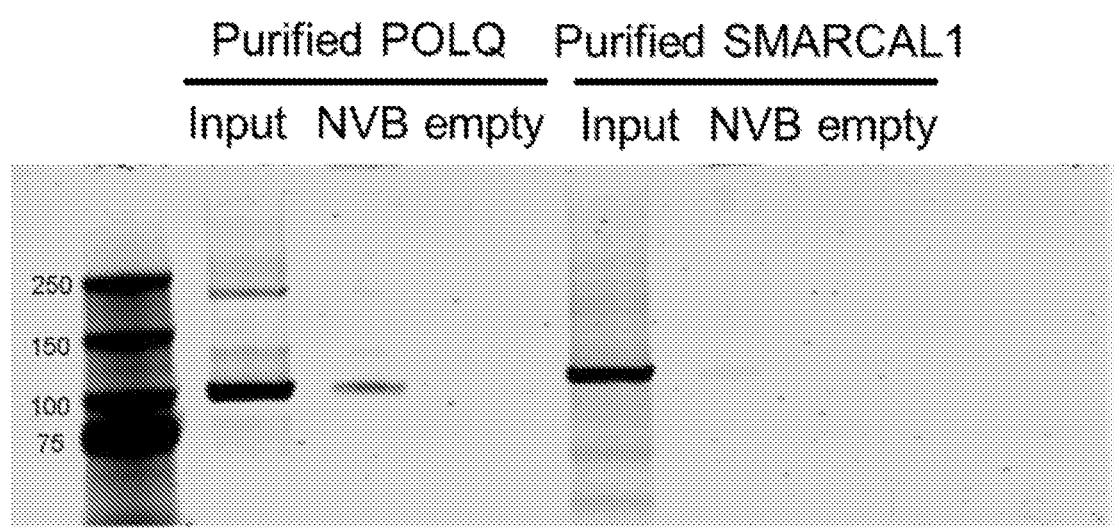
FIG. 15 contain an image of a gel showing that novobiocin specifically binds to POLQ ATPase domain.

An image shown in FIG. 15 shows that novobiocin specifically binds to POLQ ATPase domain. Novobiocin-conjugated beads pull down POLQ ATPase domain but not Smarcal1.

Other Embodiments

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A method of treating a homologous recombination (HR)-deficient cancer, the method comprising administering to a subject in need thereof a therapeutically effective amount of a compound of Formula (I):

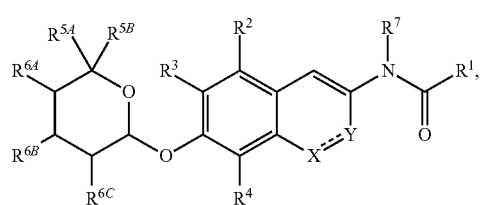

or a pharmaceutically acceptable salt thereof, wherein:
the bond ═ between X and Y is a single bond or a double bond;
X and Y are independently selected from the group consisting of: O, N, CH, and C(═O);
$R^1$ is selected from the group consisting of: $C_{1-6}$ alkyl, $C_{2-6}$ alkenyl, $C_{2-6}$ alkynyl, $C_{1-4}$ haloalkyl, $C_{6-12}$ aryl and 5-10 membered heteroaryl, each of which is optionally substituted by 1, 2, or 3 groups independently selected from the group consisting of: $Cy^1$ and $R^g$;
$R^2$ and $R^3$ are independently selected from the group consisting of: H, $C_{1-6}$ alkyl, $C_{2-6}$ alkenyl, $C_{2-6}$ alkynyl, $C_{1-4}$ haloalkyl, $C_{1-6}$ alkoxy, and $C_{1-6}$ haloalkoxy;
$R^4$ is selected from the group consisting of: H, $C_{1-6}$ alkyl, $C_{2-6}$ alkenyl, $C_{2-6}$ alkynyl, $C_{1-4}$ haloalkyl, $C_{6-12}$ aryl, and $C_{6-12}$ aryl-$C_{1-3}$ alkylene;
$R^{5A}$ and $R^{5B}$ are independently selected from the group consisting of: H and $C_{1-3}$ alkyl;
$R^{6A}$, $R^{6B}$ and $R^{6C}$ are independently selected from the group consisting of: OH, $C_{1-6}$ alkoxy, $C_{1-6}$ haloalkoxy, C(═O)NR$^{a1}$R$^{a2}$, and C(O)OR$^{a1}$;
$R^{a1}$ and $R^{a2}$ are independently selected from the group consisting of: H and $C_{1-3}$ alkyl;
$R^7$ is selected from the group consisting of: H, $C_{1-6}$ alkyl, $C_{2-6}$ alkenyl, $C_{2-6}$ alkynyl, and $C_{1-4}$ haloalkyl, each of which is optionally substituted by 1 or 2 $Cy^1$;
each $Cy^1$ is independently selected from the group consisting of: $C_{6-12}$ aryl and 5-10 membered heteroaryl, each of which is optionally substituted by 1, 2, or 3 independently selected $R^g$ groups; and
each $R^g$ is independently selected from the group consisting of: OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino and di($C_{1-6}$ alkyl)amino.

2. The method of claim 1, wherein the compound of Formula (I) is selected from the group consisting of:

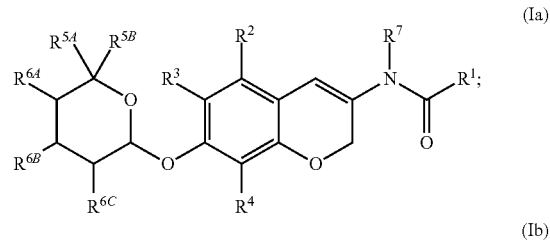

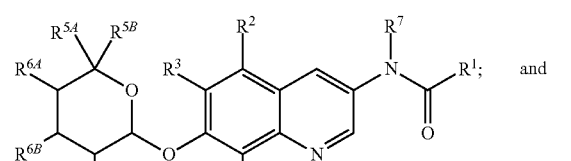

and

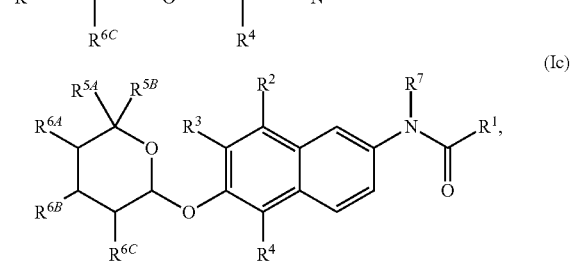

or a pharmaceutically acceptable salt thereof.

3. The method of claim 1, wherein $R^1$ is selected from the group consisting of: $C_{1-6}$ alkyl, $C_{6-12}$ aryl and 5-10 membered heteroaryl, each of which is optionally substituted by 1 or 2 groups independently selected from the group consisting of: $Cy^1$ and $R^g$.

4. The method of claim 3, wherein $R^1$ is $C_{1-6}$ alkyl.

5. The method of claim 3, wherein $R^1$ is 5-10 membered heteroaryl.

6. The method of claim 3, wherein $R^1$ is $C_{6-12}$ aryl, optionally substituted by 1 or 2 groups independently selected from the group consisting of: $Cy^1$ and $R^g$.

7. The method of claim 3, wherein $R^1$ is selected from the group consisting of: methyl, 3-(3-methylbut-2-en-1-yl)-4-hydroxyphenyl, 3',6-dimethoxy-[1,1'-biphenyl-3-yl], and indol-2-yl.

8. The method of claim 1, wherein $R^2$ and $R^3$ are independently selected from the group consisting of: H and $C_{1-6}$ alkoxy.

9. The method of claim 8, wherein $R^2$ and $R^3$ are each H.

10. The method of claim 8, wherein $R^2$ is H and $R^3$ is $C_{1-6}$ alkoxy.

11. The method of claim 8, wherein $R^2$ is $C_{1-6}$ alkoxy and $R^3$ is H.

12. The method of claim 8, wherein $R^2$ and $R^3$ are independently selected from the group consisting of: H, methoxy, propoxy, and isopropoxy.

13. The method of claim 1, wherein $R^4$ is selected from the group consisting of: H, $C_{1-6}$ alkyl, $C_{6-12}$ aryl, and $C_{6-12}$ aryl-$C_{1-3}$ alkylene.

14. The method of claim 13, wherein $R^4$ is selected from the group consisting of: H, methyl, ethyl, phenyl, and benzyl.

15. The method of claim 1, wherein $R^{5A}$ and $R^{5B}$ are each $C_{1-3}$ alkyl.

16. The method of claim 1, wherein $R^{5A}$ and $R^{5B}$ are each methyl.

17. The method of claim 1, wherein $R^{6A}$, $R^{6B}$ and $R^{6C}$ are independently selected from the group consisting of: OH, $C_{1-6}$ alkoxy, and $C(=O)NR^{a1}R^{a2}$.

18. The method of claim 17, wherein $R^{6A}$ is $C_{1-6}$ alkoxy.

19. The method of claim 17, wherein $R^{6B}$ is selected from the group selected from: OH and $C(=O)NR^{a1}R^{a2}$.

20. The method of claim 19, wherein $R^{6B}$ is selected from the group selected from: OH and $C(=O)NH_2$.

21. The method of claim 17, wherein $R^{6C}$ is OH.

22. The method of claim 1, wherein $R^7$ is selected from the group consisting of: H and $C_{1-6}$ alkyl, wherein the $C_{1-6}$ alkyl is optionally substituted with $Cy^1$.

23. The method of claim 22, wherein $R^7$ is selected from the group consisting of: H and 4-methoxybenzyl.

24. The method of claim 22, wherein $R^7$ is H.

25. The method of any claim 1, wherein $Cy^1$ is $C_{6-12}$ aryl, optionally substituted by 1 or 2 independently selected $R^g$ groups.

26. The method of claim 25, wherein $Cy^1$ is phenyl, optionally substituted with $R^g$.

27. The method of claim 25, wherein $Cy^1$ is selected from the group consisting of: 3-methoxyphenyl and 4-methoxyphenyl.

28. The method of claim 1, wherein $R^g$ is selected from the group consisting of: OH, $C_{2-6}$ alkenyl, and $C_{1-6}$ alkoxy.

29. The method of claim 28, wherein $R^g$ is selected from the group consisting of: OH, 3-methylbut-2-en-1-yl, and methoxy.

30. The method of claim 1, wherein:
$R^1$ is selected from the group consisting of: $C_{1-6}$ alkyl, $C_{6-12}$ aryl and 5-10 membered heteroaryl, each of which is optionally substituted by 1 or 2 groups independently selected from the group consisting of: $Cy^1$ and $R^g$;
$R^2$ and $R^3$ are independently selected from the group consisting of: H and $C_{1-6}$ alkoxy;

$R^4$ is selected from the group consisting of: H, $C_{1-6}$ alkyl, $C_{6-12}$ aryl, and $C_{6-12}$ aryl-$C_{1-3}$ alkylene;
$R^{5A}$ and $R^{5B}$ are each $C_{1-3}$ alkyl;
$R^{6A}$, $R^{6B}$ and $R^{6C}$ are independently selected from the group consisting of: OH, $C_{1-6}$ alkoxy, and $C(=O)NR^{a1}R^{a2}$;
$R^1$ is selected from the group consisting of: H and $C_{1-6}$ alkyl, wherein the $C_{1-6}$ alkyl is optionally substituted with $Cy^1$;
$Cy^1$ is $C_{6-12}$ aryl, optionally substituted by 1 or 2 independently selected $R^g$ groups; and
$R^g$ is selected from the group consisting of: OH, $C_{2-6}$ alkenyl, and $C_{1-6}$ alkoxy.

31. The method of claim 1, wherein:
$R^1$ is selected from the group consisting of: methyl, indol-2-yl, and phenyl, wherein the phenyl is optionally substituted by 1 or 2 groups independently selected from the group consisting of: $Cy^1$ and $R^g$;
$R^2$ and $R^3$ are independently selected from the group consisting of: H, methoxy, propoxy, and isopropoxy;
$R^4$ is selected from the group consisting of: H, methyl, ethyl, phenyl, and benzyl;
$R^{5A}$ and $R^{5B}$ are each methyl;
$R^{6A}$ is $C_{1-6}$ alkoxy;
$R^{6B}$ is selected from the group selected from: OH and $C(=O)NH_2$;
$R^{6C}$ is OH;
$R^1$ is selected from the group consisting of: H and $C_{1-6}$ alkyl substituted with $Cy^1$;
$Cy^1$ is phenyl, optionally substituted with $R^g$; and
$R^g$ is selected from the group consisting of: OH, 3-methylbut-2-en-1-yl, and methoxy.

32. The method of claim 1, wherein the compound of Formula (I) is selected from the group consisting of:

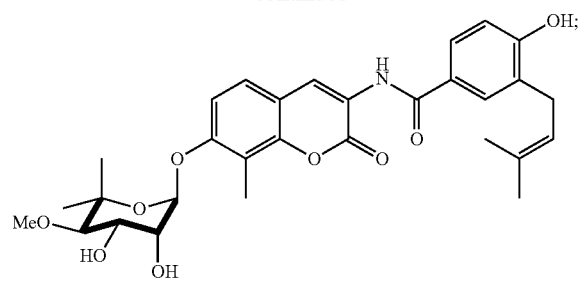
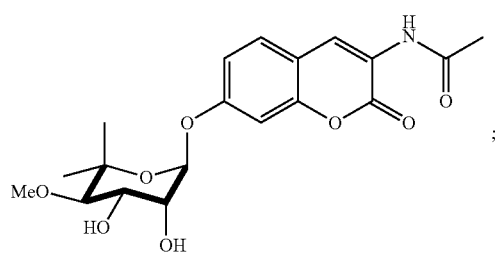
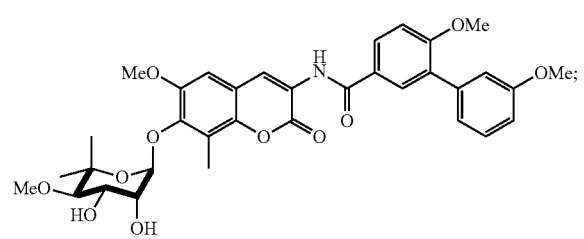
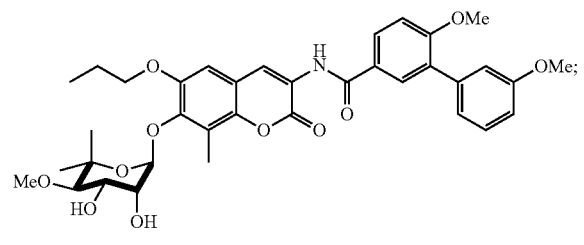
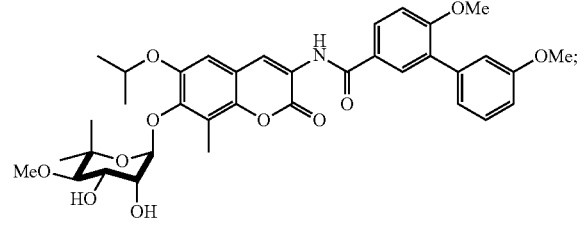
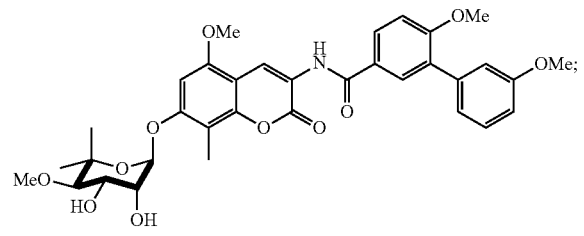
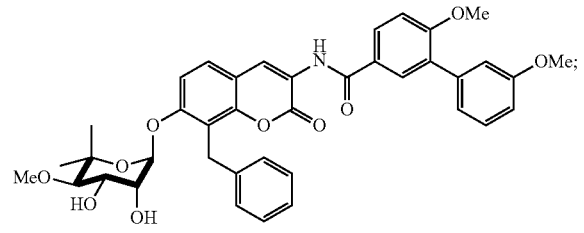
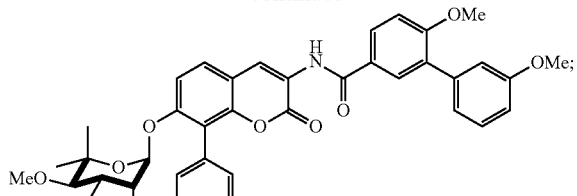
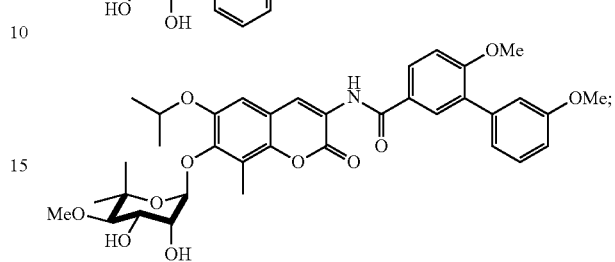
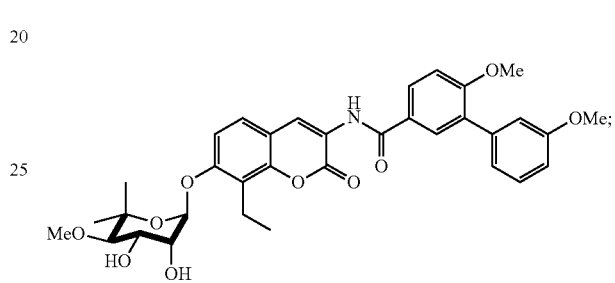
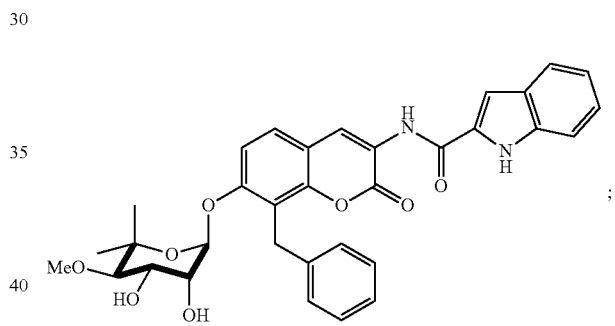
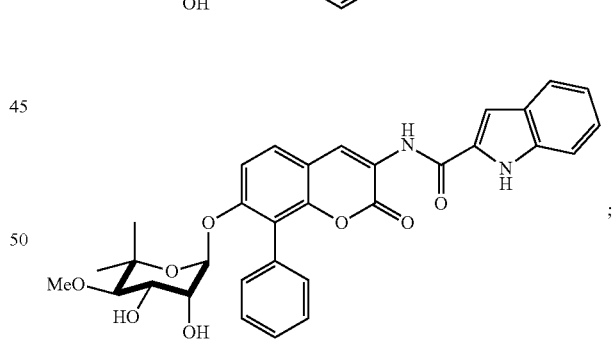
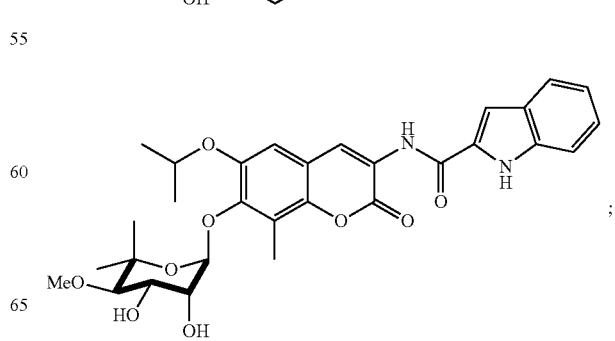

-continued

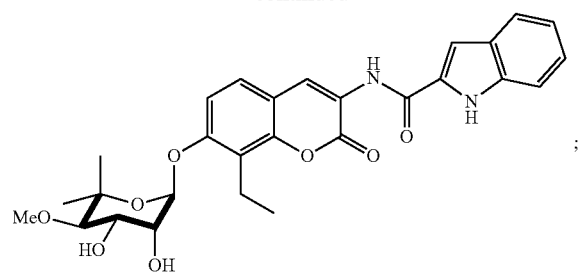
;

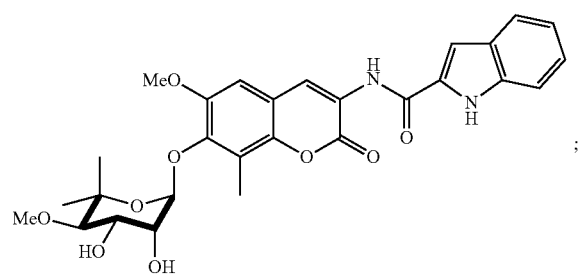
;

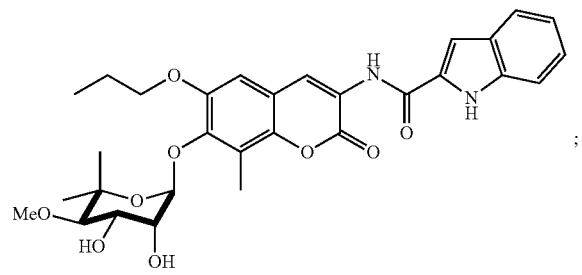
;

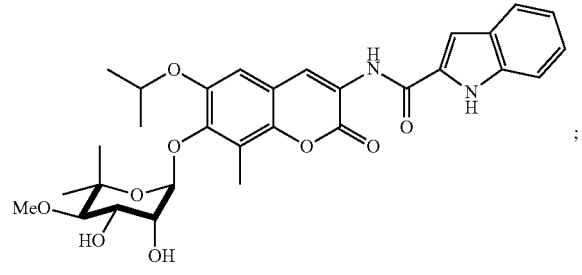
;

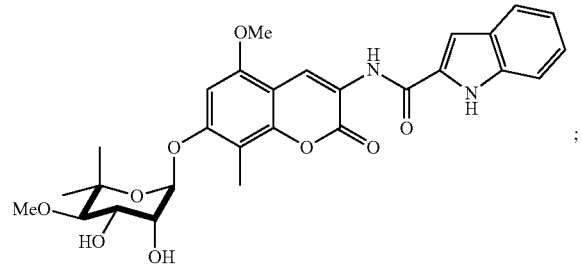
;

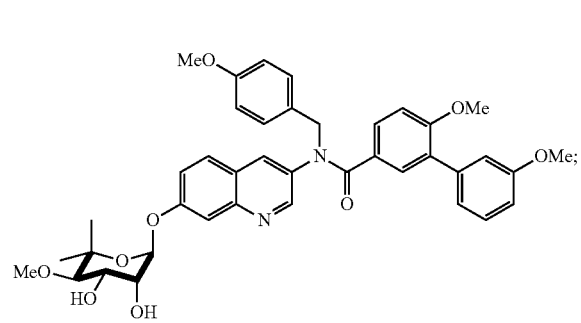

-continued

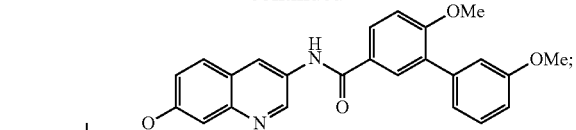
;

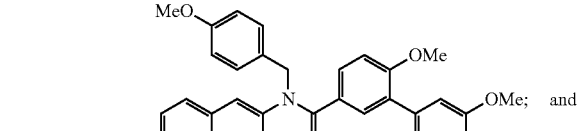
; and

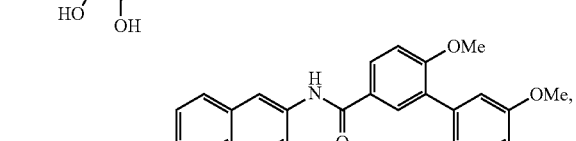
, or a pharmaceutically acceptable salt thereof.

33. The method of claim 1, further comprising, before administering the compound to the patient, determining that the HR-deficient cancer contains a mutation or an alteration in a gene regulating homologous recombination.

34. The method of claim 33, wherein the gene regulating homologous recombination is BRCA1/2.

35. The method of claim 1, wherein the cancer is selected from prostate cancer, colon cancer, lung cancer, liver cancer, sarcoma, melanoma, breast cancer, ovarian cancer, and pancreatic cancer.

36. A method of treating a cancer selected from ovarian cancer and pancreatic cancer, the method comprising administering to a subject in need thereof a therapeutically effective amount of a compound of Formula (I):

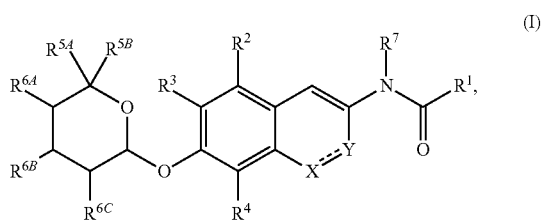

or a pharmaceutically acceptable salt thereof, wherein:
the bond === between X and Y is a single bond or a double bond;
X and Y are independently selected from the group consisting of: O, N, CH, and C(=O);
$R^1$ is selected from the group consisting of: $C_{1-6}$ alkyl, $C_{2-6}$ alkenyl, $C_{2-6}$ alkynyl, $C_{1-4}$ haloalkyl, $C_{6-12}$ aryl and 5-10 membered heteroaryl, each of which is optionally substituted by 1, 2, or 3 groups independently selected from the group consisting of: $Cy^1$ and $R^g$;

$R^2$ and $R^3$ are independently selected from the group consisting of: H, $C_{1-6}$ alkyl, $C_{2-6}$ alkenyl, $C_{2-6}$ alkynyl, $C_{1-4}$ haloalkyl, $C_{1-6}$ alkoxy, and $C_{1-6}$ haloalkoxy;

$R^4$ is selected from the group consisting of: H, $C_{1-6}$ alkyl, $C_{2-6}$ alkenyl, $C_{2-6}$ alkynyl, $C_{1-4}$ haloalkyl, $C_{6-12}$ aryl, and $C_{6-12}$ aryl-$C_{1-3}$ alkylene;

$R^{5A}$ and $R^{5B}$ are independently selected from the group consisting of: H and $C_{1-3}$ alkyl;

$R^{6A}$, $R^{6B}$ and $R^{6C}$ are independently selected from the group consisting of: OH, $C_{1-6}$ alkoxy, $C_{1-6}$ haloalkoxy, $C(=O)NR^{a1}R^{a2}$, and $C(O)OR^{a1}$;

$R^{a1}$ and $R^{a2}$ are independently selected from the group consisting of: H and $C_{1-3}$ alkyl;

$R^7$ is selected from the group consisting of: H, $C_{1-6}$ alkyl, $C_{2-6}$ alkenyl, $C_{2-6}$ alkynyl, and $C_{1-4}$ haloalkyl, each of which is optionally substituted by 1 or 2 $Cy^1$;

each $Cy^1$ is independently selected from the group consisting of: $C_{6-12}$ aryl and 5-10 membered heteroaryl, each of which is optionally substituted by 1, 2, or 3 independently selected $R^g$ groups; and each $R^g$ is independently selected from the group consisting of: OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino and di($C_{1-6}$ alkyl)amino.

37. The method of claim 1, further comprising administering to the subject a therapeutically effective amount of an additional anti-cancer agent.

38. The method of claim 37, wherein the additional anti-cancer agent is a platinum-based anti-cancer agent.

39. The method of claim 38, wherein the platinum-based anti-cancer agent is selected from carboplatin and cisplatin.

40. The method of claim 37, wherein the additional anti-cancer agent is a PARP inhibitor.

41. The method of claim 40, wherein the PARP inhibitor is selected from olaparib, veliparib, BGB-290, talazoparib, BMN 673, and niraparib.

42. A method of inhibiting DNA polymerase θ (Polθ) in a homologous recombination (HR)-deficient cancer cell, the method comprising contacting the HR-deficient cancer cell with an effective amount of a compound of Formula (I):

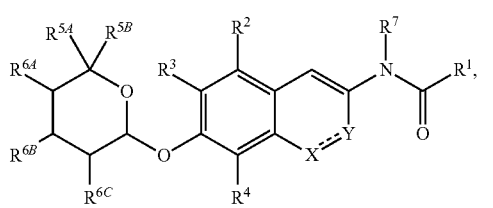

(I)

or a pharmaceutically acceptable salt thereof, wherein:

the bond $=$ between X and Y is a single bond or a double bond;

X and Y are independently selected from the group consisting of: O, N, CH, and C(=O);

$R^1$ is selected from the group consisting of: $C_{1-6}$ alkyl, $C_{2-6}$ alkenyl, $C_{2-6}$ alkynyl, $C_{1-4}$ haloalkyl, $C_{6-12}$ aryl and 5-10 membered heteroaryl, each of which is optionally substituted by 1, 2, or 3 groups independently selected from the group consisting of: $Cy^1$ and $R^g$;

$R^2$ and $R^3$ are independently selected from the group consisting of: H, $C_{1-6}$ alkyl, $C_{2-6}$ alkenyl, $C_{2-6}$ alkynyl, $C_{1-4}$ haloalkyl, $C_{1-6}$ alkoxy, and $C_{1-6}$ haloalkoxy;

$R^4$ is selected from the group consisting of: H, $C_{1-6}$ alkyl, $C_{2-6}$ alkenyl, $C_{2-6}$ alkynyl, $C_{1-4}$ haloalkyl, $C_{6-12}$ aryl, and $C_{6-12}$ aryl-$C_{1-3}$ alkylene;

$R^{5A}$ and $R^{5B}$ are independently selected from the group consisting of: H and $C_{1-3}$ alkyl;

$R^{6A}$, $R^{6B}$ and $R^{6C}$ are independently selected from the group consisting of: OH, $C_{1-6}$ alkoxy, $C_{1-6}$ haloalkoxy, $C(=O)NR^{a1}R^{a2}$, and $C(O)OR^{a1}$;

$R^{a1}$ and $R^{a2}$ are independently selected from the group consisting of: H and $C_{1-3}$ alkyl;

$R^7$ is selected from the group consisting of: H, $C_{1-6}$ alkyl, $C_{2-6}$ alkenyl, $C_{2-6}$ alkynyl, and $C_{1-4}$ haloalkyl, each of which is optionally substituted by 1 or 2 $Cy^1$;

each $Cy^1$ is independently selected from the group consisting of: $C_{6-12}$ aryl and 5-10 membered heteroaryl, each of which is optionally substituted by 1, 2, or 3 independently selected $R^g$ groups; and each $R^g$ is independently selected from the group consisting of: OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino and di($C_{1-6}$ alkyl)amino.

43. The method of claim 42, wherein the cancer cell is contacted in vitro.

44. The method of claim 42, wherein the cancer cell is contacted in vivo.

45. The method of claim 42, wherein the cancer cell is contacted ex vivo.

* * * * *